(12) United States Patent
Tanaka et al.

(10) Patent No.: US 6,689,339 B1
(45) Date of Patent: Feb. 10, 2004

(54) VISCOUS COMPOSITIONS CONTAINING CARBON DIOXIDE

(75) Inventors: Masaya Tanaka, Kobe (JP); Masato Hiki, Osaka (JP)

(73) Assignee: Medion Research Laboratories Inc., Kobe (JP)

( * ) Notice: Subject to any disclaimer, the term of this patent is extended or adjusted under 35 U.S.C. 154(b) by 0 days.

(21) Appl. No.: 09/530,731

(22) PCT Filed: Oct. 5, 1998

(86) PCT No.: PCT/JP98/04503

§ 371 (c)(1),
(2), (4) Date: Aug. 17, 2000

(87) PCT Pub. No.: WO99/24043

PCT Pub. Date: May 20, 1999

(30) Foreign Application Priority Data

Nov. 7, 1997 (JP) .............................. 9-305151

(51) Int. Cl.⁷ .............................. A61K 9/46; A61K 7/48; A61L 9/04; A61L 9/015; A01N 25/16
(52) U.S. Cl. .......................... 424/44; 424/401; 424/464; 424/466; 424/43; 424/700; 424/78.03; 514/817; 514/828; 514/858; 514/887; 514/944; 514/945; 514/947; 514/960
(58) Field of Search ........................... 424/44, 401, 464, 424/466, 43, 78.03, 700; 514/817, 828, 858, 887, 944, 945, 947, 960

(56) References Cited

U.S. PATENT DOCUMENTS

| | | | | |
|---|---|---|---|---|
| 4,289,751 A | * | 9/1981 | Windheuser | 424/44 |
| 4,487,757 A | | 12/1984 | Kiozpeoplou | |
| 5,100,674 A | | 3/1992 | Ser et al. | |

FOREIGN PATENT DOCUMENTS

| | | |
|---|---|---|
| EP | 01172319 | 7/1989 |
| EP | 0 362 655 | 4/1990 |
| EP | 0 380 253 | 8/1990 |
| EP | 0467776 | 1/1992 |
| GB | 702952 | 1/1954 |
| JP | 59106415 | 6/1984 |
| JP | 61-207322 | 9/1986 |
| JP | 61-293374 | 12/1986 |
| JP | 62-181219 | 8/1987 |
| JP | 62-286922 | 12/1987 |
| JP | 63-267724 | 11/1988 |
| JP | 4-312521 | 11/1992 |
| JP | 5229933 | 9/1993 |
| JP | 9-206001 | 8/1997 |
| WO | WO 9014070 | 11/1990 |
| WO | 9619189 | 6/1996 |

OTHER PUBLICATIONS

Mori et al, Foamable Cosmetics, Dec. 19, 1988, JP 63310807 A, See: abstract.*
Mori et al., Foamable Cosmetic, PTO 02–4021 translation of Japanese Kokai Patent Application No. Sho 63[1988]–310807, entire reference.*
Remington's Pharmaceutical Sciences, Eighteenth Edition, (1990), pp. 1305.*

* cited by examiner

Primary Examiner—Frederick Krass
Assistant Examiner—Clinton Ostrup
(74) Attorney, Agent, or Firm—Armstrong, Kratz, Quintos, Hanson & Brooks, LLP

(57) ABSTRACT

A carbon dioxide-containing viscous composition wherein carbon dioxide bubbles are retained in an aqueous viscous composition. Use of the composition makes it possible to treat or ameliorate itching accompanying mucocutaneous diseases or mucocutaneous disorders, mucocutaneous injury, dental diseases, skin ulcer, cryesthesia and numbness caused by peripheral circulatory disorders, musculoskeletal diseases, nervous system diseases, keratosis, constipation, unwanted hair re-growing after depilation, cosmetic troubles in the skin or hair, partial obesity, etc. while exerting little side effects.

11 Claims, No Drawings

VISCOUS COMPOSITIONS CONTAINING CARBON DIOXIDE

TECHNICAL FIELD

Thee present invention relates to a carbon dioxide-containing viscous composition which is capable of treating or ameliorating itching accompanying mucocutaneous diseases or mucocutaneous disorders such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain; mucocutaneous injuries such as decubitus ulcer, wound, burn, angular stomatitis, stomatitis, skin ulcer, rhagades, erosion, chilblain and gangrene; incomplete takes of skin graft, skin flap, etc.; dental diseases such as gingivitis, alveolar pyorrhea, denture ulcer, nigricans gingiva, stomatitis; skin ulcer, cryesthesia and numbness caused by peripheral circulatory disorders such as thromboangitis obliterans, arteriolosclerosis obliterans, diabetic peripheral circulatory disorder and varicosis in lower extremity; musculoskeletal diseases such as chronic rheumatoid arthritis, cervico-omo-brachial syndrome, myalgia, arthralgia and lumbago; nervous system diseases such as neuralgia, polyarthritis and subcute myelo-optic neuropathy; keratoses such as psoriasis, corn, callosity, ichthyosis, palmoplantar keratoderma, lichen and pityriasis; suppurative dermopathies such as acne vulgaris, impetigo, folliculitis, carbuncle, furunculosis, phlegmon, pyoderma and suppurative eczema; constipation caused by loss of reflection of defecation; suppression of hair re-growth after depilation (treatment of unwanted hair); cosmetic troubles in the skin or hair such as freckles, rough skin, muddy complexion, faded skin complexion and loss of hair glossiness, etc. with little side effects as well as of slimming a desired part of the body, and to prophylactic and therapeutic methods using the composition.

BACKGROUND ART

Antihistamines and antiallergics for external application are typically used in a topical therapy for itching. Such drugs are used when itching occurs and work to suppress the itching temporarily to a certain degree. Itching associated with eczema is generally treated with non-steroidal anti-inflammatory drugs or steroidal drugs for external application which prevent the itching by suppressing inflammation.

However, the antihistamines and antiallergics for external application are barely effective in treating itching accompanying atopic dermatitis, athlete's foot and insect bite. The non-steroidal anti-inflammatory drugs and steroidal drugs for external application do not effect satisfactorily nor immediately on itching. Further, the steroidal drugs are difficult to use because of the serious side effects.

The present invention provides a preparation effective for the treatment of itching accompanying mucocutaneous diseases or mucocutaneous disorders such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain and therapeutic and prophylactic methods using the preparation.

Further, the invention provides a preparation effective for the treatment of mucocutaneous injuries such as decubitus ulcer, wound, burn, angular stomatitis, stomatitis, skin ulcer, rhagades, erosion, chilblain and gangrene; incomplete takes of skin graft, skin flap, etc.; dental diseases such as gingivitis, alveolar pyorrhea, denture ulcer, nigricans gingiva, stomatitis; skin ulcer, cryesthesia and numbness caused by peripheral circulatory disorders such as thromboangitis obliterans, arteriolosclerosis obliterans, diabetic peripheral circulatory disorder and varicosis in lower extremity; musculoskeletal diseases such as chronic rheumatoid arthritis, cervico-omo-brachial syndrome, myalgia, arthralgia and lumbago: nervous system diseases such as neuralgia, polyarthritis and subcute myelo-optic neuropathy; keratoses such as psoriasis, corn, callosity, ichthyosis, palmoplantar keratoderma, lichen and pityriasis; suppurative dermopathies such as acne vulgaris, impetigo, folliculitis, carbuncle, furunculosis, phlegmon, pyoderma and suppurative eczema; constipation caused by loss of reflection of defecation; suppression of hair re-growth after depilation (treatment of unwanted hair); cosmetic troubles in the skin or hair such as freckles, rough skin, muddy complexion, faded skin complexion, loss of hair glossiness, etc. and partial obesity, and prophylactic and therapeutic methods using the preparation.

DISCLOSURE OF INVENTION

The inventors accomplished the present invention as a result of an extensive research wherein they found that a carbon dioxide-containing viscous composition is effective in treating itching which had not been cured by antihistamines, anti-allergics, non-steroidal anti-inflammatory drugs, steroidal drugs for external application or the like and that the composition has an anti-inflammatory action, wound healing accelerating action, skin treatment action, action for resolving partial obesity, transdermal or transmucosal drug absorption promoting action and the like.

The invention relates to the following items 1–48.

1. A carbon dioxide-containing viscous composition comprising an aqueous viscous composition containing one or more thickeners and carbon dioxide, wherein the aqueous viscous composition comprises the carbon dioxide in the form of bubbles.
2. The carbon dioxide-containing viscous composition according to item 1, which is characterized in that the thickener comprises one or more selected from the group consisting of natural polymers, semi-synthetic polymers, synthetic polymers and inorganic substances.
3. The carbon dioxide-containing viscous composition according to item 1 or 2, which is characterized in that the natural polymer used as a thickener is at least one selected from the group consisting of gum arabic, carrageenan, galactan, agar, quince seed gum, guar gum, tragacanth gum, pectin, mannan, locust bean gum, wheat starch, rice starch, corn starch, potato starch, curdlan, xanthan gum, succinoglucan, dextran, hyaluronic acid, pullulan, albumin, casein, collagen, gelatin and fibroin; the semi-synthetic polymer used as a thickener is at least one selected from the group consisting of ethyl cellulose, carboxymethyl cellulose and salts thereof, carboxymethylethyl cellulose and salts thereof, carboxymethyl starch and salts thereof, croscarmellose and salts thereof, crystalline cellulose, cellulose acetate, cellulose acetate phthalate, hydroxyethyl cellulose, hydroxypropyl cellulose, hydroxypropylmethyl cellulose, hydroxypropylmethyl cellulose phthalate, powdered cellulose, methyl cellulose, methylhydroxypropyl cellulose, pregelatinized starch, partially pregelatinized starch, carboxymethyl starch, dextrin, methyl starch, sodium alginate, propyleneglycol alginate, sodium chondroitin sulfate and sodium hyaluronate; the synthetic polymer used as a thickener is at least one selected from the group consisting of carboxyvinyl polymer, sodium polyacrylate, polyvinylacetaldiethylaminoacetate, polyvinyl alcohol, polyvinyl pyrrolidone, methacrylic acid-ethyl acrylate copolymer, methacrylic acid-ethyl methacrylate copolymer, ethyl methacrylate.trimethylammoniumethyl chloride methacrylate copolymer, dimethylaminoethyl methacrylate.methyl methacrylate copolymer; the inorganic substance used as a thickener is at least one selected from the group consisting of silicon dioxide hydrate, light anhydrous silicic acid, colloidal alumina, bentonite and laponite.

4. The carbon dioxide-containing viscous composition according to any one of items 1–3, which is characterized in that the carbon dioxide is produced by reacting an acid or acids with a carbonate or carbonates.

5. The carbon dioxide-containing viscous composition according to item 4, which is characterized in that the acid is at least one selected from the group consisting of formic acid, acetic acid, propionic acid, butyric acid, valeric acid, oxalic acid, malonic acid, succinic acid, glutaric acid, adipic acid, pimelic acid, fumaric acid, maleic acid, phthalic acid, isophthalic acid, terephthalic acid, glutamic acid, asparagic acid, glycolic acid, malic acid, tartaric acid, citric acid, lactic acid, hydroxyacrylic acid, α-oxybutric acid, glyceric acid, tartronic acid, salicylic acid, gallic acid, tropic acid, ascorbic acid, gluconic acid, phosphoric acid, potassium dihydrogenphosphate, sodium dihydrogenphosphate, sodium sulfite, potassium sulfite, sodium pyrosulfite, potassium pyrosulfite, acid sodium hexamethaphosphate, acid potassium hexamethaphosphate, acid sodium pyrophosphate, acid potassium pyrophosphate and sulfamic acid; and the carbonate is at least one selected from the group consisting of ammonium carbonate, potassium carbonate, calcium carbonate, sodium carbonate, sodium bicarbonate, potassium bicarbonate, potassium sesquicarbonate, calcium sesquicarbonate and sodium sesquicarbonate.

6. A kit comprising a carbonate or carbonates, an acid or acids, a thickener or thickeners and water in a state where the components produce substantially no carbon dioxide, which enables to produce a carbon dioxide-containing viscous composition comprising carbon dioxide bubbles by mixing the carbonate or carbonates, the acid or acids, the thickener or thickeners and water.

7. The kit according to item 6, comprising a carbonate-containing aqueous viscous composition and an acid or acids.

8. The kit according to item 6, comprising an acid-containing aqueous viscous composition and a carbonate or carbonates.

9. The kit according to item 6, comprising a carbonate-containing aqueous viscous composition and a granular (fine-granular or powdery) acid or acids.

10. The kit according to item 6, comprising an acid-containing aqueous viscous composition and a granular (fine-granular or powdery) carbonate or carbonates.

11. The kit according to item 6, comprising a carbonate-containing aqueous viscous composition and an acid-containing aqueous viscous composition.

12. The kit according to item 6, comprising a composite granule (fine-granular or powdery) of a carbonate or carbonates and an acid or acids and an aqueous viscous composition.

13. The kit according to item 6, comprising a carbonate-containing aqueous viscous composition and an acid-containing sheet.

14. The kit according to item 6, comprising an acid-containing aqueous viscous composition and a carbonate-containing sheet.

15. The kit according to item 6, comprising a carbonate or carbonates, an acid or acids and aqueous viscous composition.

16. The kit according to item 6, comprising an aqueous viscous composition and sheet containing a composite granule (fine-granular or powdery) of carbonate and acid.

17. The kit according to item 6, comprising a carbonate or carbonates, an acid or acids, a thickener or thickeners and water.

18. A pharmaceutical composition comprising, as an active ingredient, the carbon dioxide-containing viscous composition according to any one of items 1–5 or the carbon dioxide-containing viscous composition obtainable by the kit according to any one of items 6–17.

19. The pharmaceutical composition according to item 18, which is a prophylactic or therapeutic drug for itching accompanying mucocutaneous diseases or mucocutaneous disorders.

20. The pharmaceutical composition according to item 18, which is a prophylactic or therapeutic drug for skin ulcer, cryesthesia and numbness caused by peripheral circulatory disorders.

21. The pharmaceutical composition according to item 18, which is a prophylactic or therapeutic drug for dental diseases.

22. The pharmaceutical composition according to item 18, which is a prophylactic or therapeutic drug for mucocutaneous injuries.

23. The pharmaceutical composition according to item 18, which is a prophylactic or therapeutic drug for suppurative dermopathies.

24. The pharmaceutical composition according to item 18, which is a prophylactic or therapeutic drug for keratosis.

25. The pharmaceutical composition according to item 18, which is a prophylactic or therapeutic drug for musculoskeletal diseases.

26. The pharmaceutical composition according to item 18, which is a prophylactic or therapeutic drug for nervous system diseases.

27. Cosmetics comprising the carbon dioxide-containing viscous composition according to any one of items 1–5 or the carbon dioxide-containing viscous composition obtainable by the kit according to any one of items 6–17.

28. The cosmetics according to item 27, being capable of reducing or attenuating freckles.

29. Slimming cosmetics according to item 27, being capable of ameliorating partial obesities in the face, foot, arm, abdomen, latus, back, neck, chin and the like.

30. The cosmetics according to item 27, having an action of ameliorating skin complexion.

31. The cosmetics according to item 27, having an action of suppressing hair re-growth after depilation.

32. A prophylactic or therapeutic method for diseases or disorders, comprising applying to a patient an effective amount of the carbon dioxide-containing viscous composition according to any one of items 1–5 or the carbon dioxide-containing viscous compositions obtainable by the kit according to any one of items 6–17.

33. The prophylactic or therapeutic method according to item 32, wherein the diseases or disorders are mucocutaneous diseases or mucocutaneous disorders accompanied by itching.

34. The prophylactic or therapeutic method according to item 33, wherein the mucocutaneous diseases or mucocutaneous disorders accompanied by itching are athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, chilblain, rhagades and erosion.

35. The prophylactic or therapeutic method according to item 32, wherein the diseases or disorders are mucocutaneous injuries.
36. The prophylactic or therapeutic method according to item 35, wherein the mucocutaneous injuries are decubitus ulcer, wound, burn, angular stomatitis, stomatitis, skin ulcer, rhagades, erosion, chilblain and gangrene.
37. The prophylactic or therapeutic method according to item 32, wherein the diseases or disorders are suppurative dermopathies.
38. The prophylactic or therapeutic method according to item 37, wherein the suppurative dermopathies are acne vulgaris, impetigo, folliculitis, carbuncle, furunculosis, phlegmon, pyoderma and suppurative eczema.
39. The prophylactic or therapeutic method according to item 32, wherein the diseases or disorders are keratoses.
40. The prophylactic or therapeutic method according to item 39, wherein the keratoses are psoriasis, corn, callosity, ichthyosis, palmoplantar keratoderma, lichen and pityriasis.
41. The prophylactic or therapeutic method according to item 32, wherein the diseases or disorders are musculoskeletal diseases.
42. The prophylactic or therapeutic method according to item 41, wherein the musculoskeletal diseases are chronic rheumatoid arthritis, cervico-omo-brachial syndrome, myalgia, arthralgia and lumbago.
43. The prophylactic or therapeutic method according to item 32, wherein the diseases or disorders are dental diseases.
44. The prophylactic or therapeutic method according to item 43, wherein the dental diseases are gingivitis, alveolar pyorrhea, denture ulcer, nigricans gingiva and stomatitis.
45. The method for the prevention or treatment according to item 32, wherein the diseases or disorders are nervous system diseases.
46. The prophylactic or therapeutic method according to item 45, wherein the nervous system disease are neuralgia, polyarthritis and subcute myelo-optic neuropathy.
47. The prophylactic or therapeutic method according to item 32, wherein the diseases or disorders are skin ulcer, cryesthesia and numbness caused by peripheral circulatory disorders.
48. The prophylactic or therapeutic method according to item 47, wherein the peripheral circulatory disorders are thromboangitis obliterans, arteriolosclerosis obliterans, diabetic peripheral circulatory disorder and varicosis in lower extremity.

Examples of the mucocutaneous diseases or mucocutaneous disorders accompanied by itching are athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion, chilblain and the like.

Examples of the mucocutaneous injuries are decubitus ulcer, wound, burn, angular stomatitis, stomatitis, skin ulcer, rhagades, erosion, chilblain, gangrene and the like.

Examples of the suppurative dermopathies are acne vulgaris, impetigo, folliculitis, carbuncle, furunculosis, phlegmon, pyoderma, suppurative eczema and the like.

Examples of the keratoses are psoriasis, corn, callosity, ichthyosis, palmoplantar keratoderma, lichen, pityriasis and the like.

Examples of the musculoskeletal diseases are chronic rheumatoid arthritis, cervico-omo-brachial syndrome, myalgia, arthralgia, lumbago and the like.

Examples of the dental diseases are gingivitis, alveolar pyorrhea, denture ulcer, nigricans gingiva, stomatitis and the like.

Examples of the peripheral circulatory disorders which cause skin ulcer, cryesthesia and numbness are thromboangitis obliterans, arteriolosclerosis obliterans, diabetic peripheral circulatory disorder, varicosis in lower extremity and the like.

Examples of the nervous system diseases are neuralgia, polyarthritis, subcute myelo-optic neuropathy and the like.

The cosmetics have various actions of whitening, ameliorating skin complexion, ameliorating freckles, partial slimming, suppressing hair re-growth after depilation, ameliorating glossiness of hair and the like, and may be used in the form of cream, gel, paste, cleansing foam, face pack, face mask and the like.

The "aqueous viscous composition" of the present invention is a composition containing one or more thickeners dissolved in water or swollen with water. The composition is capable of retaining carbon dioxide bubbles in such a volume that carbon dioxide is supplied to the subcutaneous tissue and so on when the composition is applied to the mucocutaneous or injured skin tissue. The composition to be used is not limited as long as it can retain carbon dioxide in the form of bubbles. The composition may contain any thickeners which are used for conventional pharmaceutical preparations, cosmetics, foods and the like without limitation, and the dosage form thereof may be any one of those typically applied for treating the mucocutaneous or injured tissue, hair, etc. such as gel, cream, paste, mousse or the like.

The present invention includes, for example, the following kits:

1) a kit comprising a carbonate-containing aqueous viscous composition and acid;
2) a kit comprising an acid-containing aqueous viscous composition and carbonate;
3) a kit comprising a carbonate-containing aqueous viscous composition and granular (fine-granular or powdery) acid;
4) a kit comprising an acid-containing aqueous viscous composition and granular (fine-granular or powdery) carbonate;
5) a kit comprising a carbonate-containing aqueous viscous composition and acid-containing aqueous viscous composition;
6) a kit comprising a composite granule (fine-granule or powder) of carbonate and acid and aqueous viscous composition;
7) a kit comprising a carbonate-containing aqueous viscous composition and acid-containing sheet;
8) a kit comprising an acid-containing aqueous viscous composition and carbonate-containing sheet;
9) a kit comprising a carbonate, acid and aqueous viscous composition;
10) a kit comprising an aqueous viscous composition and sheet containing the composite granule (fine-granule or powder) of carbonate and acid; and 11) a kit comprising a carbonate, acid, water and thickener.

The composition of the present invention containing carbon dioxide bubbles can be produced by mixing the components comprised in any one of the kits before use.

As the thickener, a natural polymer, semi-synthetic polymer, synthetic polymer, inorganic substance or the like, for example, may be used alone or in combination of two or more.

The natural polymer may be, for example, a plant-derived polymer, microorganism-derived polymer and proteinaceous polymer.

The semi-synthetic polymer may be, for example, a cellulosic polymer, starch polymer, alginate polymer and other polysaccharide polymers.

Examples of the plant-derived polymer included in the natural polymer to be used as a thickener in the invention are gum arabic, carrageenan, galactan, agar, quince seed gum, guar gum, tragacanth gum, pectin, mannan, locust bean gum, wheat starch, rice starch, corn starch, potato starch and the like.

Examples of the microorganism-derived polymer included in the natural polymer to be used as a thickener in the invention are curdlan, xanthan gum, succinoglucan, dextran, hyaluronic acid, pullulan and the like.

Examples of the proteinaceous polymer included in the natural polymer to be used as a thickener in the invention are albumin, casein, collagen, gelatin, fibroin and the like.

Examples of the cellulosic polymer included in the semi-synthetic polymer to be used as a thickener in the invention are ethyl cellulose, carboxymethyl cellulose and salts thereof, carboxymethylethyl cellulose and salts thereof, carboxymethyl starch and salts thereof, croscarmellose and salts thereof, crystalline cellulose, cellulose acetate, cellulose acetate phthalate, hydroxyethyl cellulose, hydroxypropyl cellulose, hydroxypropylmethyl cellulose, hydroxypropylmethyl cellulose phthalate, powdered cellulose, methyl cellulose, methylhydroxypropyl cellulose and the like.

Examples of the starch polymer included in the semi-synthetic polymer to be used as a thickener in the invention are pregelatinized starch, partially pregelatinized starch, carboxymethyl starch, dextrin, methyl starch and the like.

Examples of the alginate polymer included in the semi-synthetic polymer to be used as a thickener in the invention are sodium alginate, propyleneglycol alginate and the like.

Examples of the other polysaccharides polymers included in the semi-synthetic polymer to be used as a thickener in the invention are sodium chondroitin sulfate and sodium hyaluronate and the like.

Examples of the synthetic polymer to be used as a thickener in the invention are carboxyvinyl polymer, sodium polyacrylate, polyvinylacetaldiethylaminoacetate, polyvinyl alcohol, polyvinyl pyrrolidone, methacrylic acid-ethyl acrylate copolymer, methacrylic acid-ethyl methacrylate copolymer, ethyl methacrylate.trimethylammoniumethyl chloride methacrylate copolymer, dimethylaminoethyl methacrylate.methyl methacrylate copolymer and the like.

Examples of the inorganic substance to be used as a thickener in the invention are silicon dioxide hydrate, light anhydrous silicic acid, colloidal alumina, bentonite, laponite and the like.

The carbon dioxide may be retained in the aqueous composition of the invention by means of a carbon dioxide gas bomb or the like, for example, wherein carbon dioxide is introduced directly to the composition.

In addition, it is possible to obtain the carbon dioxide-containing viscous composition by reacting substances, which produce carbon dioxide as a result of the reaction, in an aqueous viscous composition or by generating carbon dioxide at the same time with forming an aqueous viscous composition. The substances to generate carbon dioxide may be a carbonate and acid used in combination. Specifically, the following combinations can produce the viscous composition containing carbon dioxide; however, the present invention is not limited thereto and other combinations may be used as long as they are capable of forming the viscous composition retaining carbon dioxide in the form of bubbles.

1) a combination of a carbonate-containing aqueous viscous composition and acid;

2) a combination of an acid-containing aqueous viscous composition and carbonate;

3) a combination of a carbonate-containing aqueous viscous composition and granular (fine-granular or powdery) acid;

4) a combination of an acid-containing aqueous viscous composition and granular (fine-granular or powdery) carbonate;

5) a combination of a carbonate-containing aqueous viscous composition and acid-containing aqueous viscous composition;

6) a combination of a composite granule (fine-granule or powder) of carbonate and acid and aqueous viscous composition;

7) a combination of a carbonate-containing aqueous viscous composition and acid-containing sheet;

8) a combination of an acid-containing aqueous viscous composition and carbonate-containing sheet;

9) a combination of a carbonate, acid and aqueous viscous composition;

10) a combination of an aqueous viscous composition and sheet containing the composite granule (fine-granule or powder) of carbonate and acid; and 11) a combination of a carbonate, acid, water and thickener.

In addition, the carbonate-containing aqueous viscous composition, acid-containing aqueous viscous composition and aqueous viscous composition may respectively be prepared from a preparation such as a thickener-containing granular (fine-granular or powdery) carbonate or the like, a thickener-containing granular (fine-granular or powdery) acid or the like and a thickener-containing granule (fine-granule or powder) or the like. If the thickener-containing granular (fine-granular or powdery) carbonate or the like and the thickener-containing granular (fine-granular or powdery) acid or the like are prepared to be controlled-release preparations of a carbonate and acid, the prolonged action of the composition can be intensified.

The carbonate to be used in the invention may be one or more of ammonium carbonate, potassium carbonate, calcium carbonate, sodium carbonate, sodium bicarbonate, potassium sesquicarbonate, calcium sesquicarbonate and sodium sesquicarbonate and potassium bicarbonate.

The acid to be used in the invention may be either of organic acid or inorganic acid, which are used alone or in combination of two or more.

Examples of the organic acid are straight chain fatty acids such as formic acid, acetic acid, propionic acid, butyric acid and valeric acid; dicarboxylic acid such as oxalic acid, malonic acid, succinic acid, glutaric acid, adipic acid, pimelic acid, fumaric acid, maleic acid, phthalic acid, isophthalic acid, terephthalic acid; acidic amino acid such as glutamic acid and asparagic acid; oxy-acid such as glycolic acid, malic acid, tartaric acid, citric acid, lactic acid, hydroxyacrylic acid, α-oxybutric acid, glyceric acid, tartronic acid, salicylic acid, gallic acid, tropic acid, ascorbic acid and gluconic acid, etc.

Examples of the inorganic acid are phosphoric acid, potassium dihydrogenphosphate, sodium dihydrogenphosphate, sodium sulfite, potassium sulfite, sodium pyrosulfite, potassium pyrosulfite, acid sodium hexamethaphosphate, acid potassium hexamethaphosphate, acid sodium pyrophosphate, acid potassium pyrophosphate, sulfamic acid and the like.

Various medicinal substances such as a bactericide, antibiotics, fungicide, anti-inflammatory drug, hemostat, local anesthetic, wound-healing accelerating agent, vasodilator, fibrinolytic, keratolytic, moisturizer, various vitamins, various hormones, antipruritic and hair root activating agent may be added to the compositions of the invention to intensify the effect or to produce synergy.

It is possible to improve the skin comfort, usability and the like of the composition by adding a perfume, color material, moisturizer, oily component, surfactant, etc. and preparing the compositions in the dosage form of a cream, gel, paste, cleansing foam, face pack, face mask or the like. The perfume to be used may be one or more of a natural perfume, synthetic perfume, mixed perfume and the like.

Examples of the natural perfume are vegetable perfumes such as a rose oil, jasmine oil, neroli oil, lavender oil, ylang-ylang oil, tuberose oil, clary sage oil, clove oil, peppermint oil, geranium oil, patchouli oil, sandalwood oil, cinnamon oil, coriander oil, nutmeg oil, pepper oil, lemon oil, orange oil, bergamot oil, opoponax oil, vetiver oil, orris oil and oakmoss oil and animal oils such as a musk oil, civet oil, castoreum oil and ambergris oil.

Examples of the synthetic perfume are hydrocarbons such as limonene and β-caryophyllene; alcohols such as santalol, cis-3-hexenol, linalol, geraniol, citronellal, terpineol, bacdanol, farnesol, β-phenylethylalcohol, bramanol and menthol; aldehydes such as 2,6-nonadienal, citral, α-hexyl cinnamic aldehyde, lyral and lilial; ketones such as acetylcedrene, β-ionone, Iso E Super, irones, l-carbone, cyclopentadecanone, damascone, methyl ionones and muscone; esters such as benzylacetate, methyl dihydrojasmonate, methyl jasmonate and linalyl acetate; lactones such as β-undecalactone, jasminelactone, cyclopentadecanolide and ethylene brassylate; oxides such as anbroxane, galaxolide and rose oxide; nitrogen-containing compounds such as indole; acetals such as phenylacetaldehyde dimethylacetal; Schiff's bases such as aurantiol and the like.

Examples of the mixed perfume are animal, aldehyde, woody, oriental, citrus, chypre, spicy, green, fougere, floral, fruity and the like.

As a coloring material, an organic artificial dye, natural dye, inorganic pigment and polymer powder may be used alone or in combination of two or more.

Examples of the organic artificial dye are red dyes such as Amaranth, Erythrosine, New Coccine, Phloxine B, Rose Bengal, Acid Red, Lithol Rubin B, Lake Red, Lithol Red, Rhodamine B, Tetrachrome Tetrabromo, Brilliant Lake Red R, Deep Maroon, Toluidine Red, Tetrabromo Fluorescein, Sudan III, Helindon Pink, Fast Acid Magenta, Parmaton Red, Eosine YS, Phloxine BK, Violamine R, Brilliant Fast Scarlet, Ponceau R, Oil Red XO and Fast Red S; yellow dyes such as Tartrazine, Sunset Yellow FCF, Fluorescein, Uranine, Hansa Yellow, Pola Yellow 5G, Naphthol Yellow S, Yellow AB, Methanyl Yellow and Fast Light Yellow 3G; green dyes such as Fast Green FCF, Alizarin Cyanine Green, Quinizarin Green SS, Pyraninconque, Light Green SF Yellow, Naphthol Green B and Guinea Green B; blue dyes such as Brilliant Blue FCF, Indigo Carmine, Indigo, Patent Blue NA, Carbanthrene Blue, Alphazurine FG, Sudan Blue and Phthalo Cyanine Blue; orange dyes such as Dibromofluorescein, Permanent Orange, Benzin Orange G, Orange II, Diuodofluoresceine, Erythrosine yellow NA, Hansa Orange and Orange SS; brown dyes such as Resorcin Brown; violet dyes such as Alisarine purple and Arisrol Purple; and black dyes such as Naphtho Blue Black; etc.

Examples of the natural dye are carotenoid-based colorants such as β-carotene, β-apo-8-carotenal, capsanthin, liropin, bixin, crocin and canthaxantin; flavonoid-based colorants such as shisonin, rafanin, ninocyanine, carthamin, sufrole yellow, rutin, quercetin and cacao dye; flavine-based colorants such as liboflavine; quinone-based colorants such as laccaic acid, carminic acid, kermesic acid, alizarin, shikonin, arcanine, nichinochrome; porphyrin-based colorants such as chlorophyll and hemoglobin; diketon-based colorants such as curcumine; and betacyanizine-based dyes such as betanin; etc.

Examples of the inorganic pigment are fillers such as mica, talc, kaolin, calcium carbonate, magnesium carbonate, silicic acid anhydride, aluminium oxide and barium sulfate; coloring pigments such as red iron oxide, yellow iron oxide, black iron oxide, chromium oxide, ultramarine, iron blue and carbon black; white pigments such as titanium dioxide and zinc oxide; pearly pigments such as titanated mica, fish scale flake and bismuth oxichloride; and particularly functioning pigments such as boron nitride, photochromic pigments, synthetic fluorine gold mica and iron containing synthetic fluorine gold mica; etc.

Examples of the polymer powder are polyethylene powder, poly(methyl methacrylate), polyethylenetelephthalate.polymethylmethacrylate laminate powder, nylon powder and the like.

Examples of the moisturizer are sorbitol, glycerin, sodium lactate, sodium hyaluronate, sodium 2-pirrolydone-5-carboxylate, 1,3-butylene glycol, propylene glycol, polyethylene glycol and the like.

Examples of the oily component are oils and fats such as avocado oil, almond oil, olive oil, cacao butter, hardened palm oil, synthetic triglyceride, evening primrose oil, castor oil, sunflower oil, jojoba oil and macadamian nut oil; hydrocarbons such as squalane, ceresin, hard paraffin, microcrystalline wax, liquid paraffin and vaseline; waxes such as carnauba wax, candelilla wax, yellow bees wax and lanolin; higher alcohols such as isostearyl alcohol, 2-octyldodecanol, stearyl alcohol, cetyl alcohol, cholesterol, hexadecyl alcohol and behenyl alcohol; fatty acids such as isostearic acid, oleic acid, stearic acid, parmitic acid, behenic acid and myristic acid; synthetic esters such as isopropylmyristate, cetyl 2-ethylhexanoate, glycerin triester, cholesteryl ester, pentaerythritol tetraester, diisosteryl malate; and silicone oils such as cyclomethicon, dimethyl polysiloxane, methyl polysiloxane and methyphenyl polysiloxane; etc.

Examples of the surfactant are nonionic surfactants such as diglycerol dioleate, sorbitan fatty acid ester, glycerin monooleate, glycerin monostearate, propyleneglycol monostearate, polyoxyethylene alkylether, polyoxyethylene sorbitan fatty acid ester, polyoxyethylene.polyoxypropylene block polymer, polyoxyethylen hydrogenated castor oil; anionic surfactants such as acyl-N-methyltaurine salt, salt of alkylether phosphate ester, alkyl sodium sulfate, N-acylamino acid salt, higher fatty acid soap and polyoxyethylene alkylether sulfate; etc.

In the case of using the carbon dioxide-containing viscous composition of the invention for the therapy or prophylaxis of mucocutaneous diseases or mucocutaneous disorders or for the cosmetic purpose, the composition may be applied to a part of the body directly, by using an absorbent material such as a gauze or sponge or by patching a bag made of the absorbent material wherein the composition is filled. More enhanced efficacy is provided by employing a closure therapy in combination with the above-mentioned therapy or prophylaxis, wherein the part of the body to which the composition is applied is covered with a film of poor permeability or dressing material. It is also efficacious to bathe a part of the body in a vessel charged with the composition. In this case, prolonged efficacy is provided by resupplying carbon dioxide to the composition by using a carbon dioxide bomb or the like.

In the case of using the carbon dioxide-containing viscous composition of the invention for treating constipation, the composition may be injected to the rectum by means of a tube or syringe as is the case with an enema.

In the case of using the carbon dioxide-containing viscous composition of the invention for the treatment of stomatitis or the like, the composition may be used as a gurgle in addition to the same usage as that described in the therapy or prophylaxis of mucocutaneous diseases or mucocutaneous disorders or for the cosmetic purpose.

In the case of using the carbon dioxide-containing viscous composition of the invention for dental diseases, the composition may be administered to the periodontal pocket using a syringe or the like in treating periodontal diseases. More enhanced efficacy is provided by covering the gum around the periodontal pocket with the composition. When the composition is used for treating stomatitis or nigricans gingiva, the affected area may be covered with the composition using a syringe or spatula. When treating denture ulcer, the composition may be applied to the ulcer in an appropriate amount to cover the affected area. Satisfactory efficacy can be provided even if a denture is attached to the gum after covering the ulcer with the composition.

The carbon dioxide-containing viscous composition of the invention can be removed easily by wiping with a tissue paper, etc. or washing with water, etc. However, materials used for the composition and the composition itself are highly safety. Therefore, in a case where the composition is administered for treating the injured tissue such as decubitus ulcer, etc., no trouble will be caused even if the composition is not removed completely from the affected area. As the case may be, the composition can be applied to the affected area without removing the composition applied previously.

In the case of using the carbon dioxide-containing viscous composition of the invention for the purpose of partial slimming, the composition may be applied to the abdomen or the like when taking a bath so that the composition can be easily washed away after a predetermined time.

The carbon dioxide-containing viscous composition of the invention is effective for a therapy or prophylaxis of itching, various mucocutaneous diseases or mucocutaneous disorders or when used for the cosmetic purpose even if it is removed after being applied to the skin or mucosa for a few minutes. However, the composition is typically applied to the skin and mucosa or the injured tissue of the skin for 5 minutes or more. The composition is also effective in saving labor required for ministration, especially in treating decubitus ulcer, since the composition can be used continuously for 24 hours or more. When the composition is used for the cosmetic purpose such as an improvement of the skin complexion or the like, single administration produces an immediate effect. It is possible to enhance the cosmetic efficacy by increasing a time length of application, frequency of application and period for application. As to the partial slimming, satisfactory effect is produced by using the composition once daily for not less than a month, and the effect is enhanced by increasing a time length of application, number of times of application and period for application.

The carbon dioxide-containing viscous composition of the invention does not lose its efficacy for a long period if it is kept in a sealed vessel or the like. In addition, the composition can be used in such a manner that it is prepared before each administration. More specifically, in the case of preparing the carbon dioxide-containing viscous composition of the invention before each administration, the composition may be obtained by, for example, applying or patching a carbonate-containing aqueous viscous composition or a film or sheet of aqueous or porous polymer, followed by applying, patching or inspersing an acid-containing aqueous composition, a film or sheet of aqueous or porous polymer or granules thereon. Further, the carbon dioxide-containing viscous composition of the invention can also be obtained by fixing the granule or the like on a polymer film or polymer sheet of poor permeability using an adhesive, followed by applying the polymer film or polymer sheet over a carbonate-containing aqueous viscous composition or a film or sheet of aqueous or porous polymer. In this case, the closure therapy can be carried out more efficiently. Of course, the same effect is produced when the carbonate and acid are exchanged in the above combinations, and the carbon dioxide-containing viscous composition can be obtained by using a composite granule of carbonate and acid in combination with the aqueous viscous composition. In the preparation before each administration, the carbon dioxide-containing viscous composition is cooled down due to an endothermic reaction associated with the generation of carbon dioxide; therefore, materials to be used for the preparation or the prepared carbon dioxide-containing viscous composition may be warmed up.

The carbon dioxide-containing viscous composition of the present invention is used for treating the injured tissue and mucosa preferably at a pH of 5–8. Pain may be caused if the pH of the composition is 5 or less due to the acidic stimulation, whereas the tissue may be injured if the pH of the composition is 8 or more due to the protein denaturing action of alkali. The composition of the invention is applied to the skin without injury preferably at a pH of 3–9. Side effects such as pain or eruption may be caused if the pH of the composition is 3 or less due to the acidic stimulation to the skin, whereas the tissue may be injured if the pH of the composition is 9 or more due to the protein denaturing action of alkali.

The carbon dioxide-containing viscous composition of the invention have a water content of about 40–99 wt %, preferably about 60–96 wt %.

In the case of producing carbon dioxide using a carbonate and acid, the carbonate may be used in an amount of about 0.01–30 parts by weight and the acid may be used in an amount of about 0.01–30 parts by weight based on 100 parts by weight of the aqueous viscous composition.

The composition of the invention may retain its volume of, with setting a volume of the composition charged in a graduated cylinder immediately after the preparation as 100, typically 30 or more, preferably 50 or more, more preferably 70 or more 2 hours after the preparation.

The carbon dioxide-containing viscous composition of the invention contains carbon dioxide bubbles in an amount of about 1–99 vol %, preferably about 5–90 vol %, more preferably about 10–80 vol % in the use thereof.

The composition of the invention is capable of treating and preventing or ameliorating itching accompanying mucocutaneous diseases or mucocutaneous disorders such as athlete's foot, insect bite, atopic dermatitis, nummular eczema, xeroderma, seborrheic eczema, urticaria, prurigo, housewives' eczema, acne vulgaris, impetigo, folliculitis, carbuncle, furunculosis, phlegmon, pyoderma, psoriasis, ichthyosis, palmoplantar keratoderma, lichen, pityriasis, wound, burn, rhagades, erosion and chilblain; mucocutaneous injuries such as decubitus ulcer, wound, burn, angular stomatitis, skin ulcer, rhagades, erosion, chilblain and gangrene; incomplete takes of skin graft, skin flap, etc.; dental diseases such as gingivitis, alveolar pyorrhea, denture ulcer, nigricans gingiva, stomatitis; skin ulcer, cryesthesia and numbness caused by peripheral circulatory disorders such as thromboangitis obliterans, arteriolosclerosis obliterans, diabetic peripheral circulatory disorder and varicosis in lower extremity; musculoskeletal diseases such as chronic rheumatoid arthritis, cervico-omo-brachial syndrome, myalgia, arthralgia and lumbago; nervous system diseases such as neuralgia, polyarthritis and subcute myelo-optic neuropathy; keratoses such as psoriasis, corn, callosity, ichthyosis, palmoplantar keratoderma, lichen and pityriasis; suppurative dermopathies such as acne vulgaris, impetigo, folliculitis, carbuncle, furunculosis, phlegmon, pyoderma and suppurative eczema; constipation caused by hyporeflexia; suppression of hair re-growth after depilation (treatment of unwanted hair); cosmetic troubles in the skin or hair such as freckles, rough skin, faded skin complexion, loss of tension or brilliancy of skin, loss of hair glossiness and the like without causing side effects as well as of slimming a desired part of the body when applied thereto.

BEST MODE FOR CARRYING OUT THE INVENTION

The present invention will be described below in more detail with reference to examples. The invention, however, is not limited to the examples. In the tables shown below, the numerals are expressed in terms of "part by weight", unless otherwise specified.

Examples 1–84

Tables 1 to 7 show carbon dioxide-containing viscous compositions each preparing by mixing a carbonate-containing aqueous viscous composition and an acid.

Production Process

Carbonate-containing aqueous viscous compositions are prepared combining thickeners, purified water and carbonates as shown in Tables 1 to 7. Solid acids are used as they are or after being pulverized or dissolved or dispersed in a suitable solvent. Liquid acids are used as they are or after being diluted with a suitable solvent. The obtained carbonate-containing aqueous viscous composition and the acid are mixed to provide a carbon dioxide-containing viscous composition.

<Preparation of the Carbonate-containing Aqueous Viscous Compositions>

The thickener or thickeners are dissolved or swollen in purified water in a container such as a beaker, and the carbonate is dissolved or dispersed. If necessary, the purified water may be heated to promote dissolution or swelling of the thickeners, and the thickeners may be dissolved or dispersed in a suitable solvent before use. If necessary, suitable additives and medicinal substances may also be added.

Evaluation of the Carbon Dioxide-containing Viscous Compositions

<Foaming Property>

50 g of the carbonate-containing aqueous viscous composition and 1 g of the acid are placed in a cup 5 cm in diameter and 10 cm high to measure the volume. The mixture is stirred 20 times for 10 seconds to provide a carbon dioxide-containing viscous composition. One minute after stirring, the volume of the composition is measured to determine volume increase % as compared to the volume before stirring. The composition is evaluated for its foaming property according to the following criteria 1:

Evaluation Criteria 1>

| Increase (%) | Foaming property |
|---|---|
| 70% or more | +++ |
| 50%–70% | ++ |
| 30%–50% | + |
| 30% or less | 0 |

The volume is measured by marking the cup at the level of the carbon dioxide-containing viscous composition at the time of each measurement, removing the composition, pouring water into the cup to the level of the composition and measuring the volume of the water using a graduated cylinder.

<Persistence of Gas Bubbles>

50 g of the carbonate-containing aqueous viscous composition and 1 g of the acid are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of gas bubbles is evaluated according to the following criteria 2:

<Evaluation Criteria 2>

| Decrease (%) | Persistence of gas bubbles |
|---|---|
| 20% or less | +++ |
| 20%–40% | ++ |
| 40%–60% | + |
| 60% or more | 0 |

The volume is measured by marking the cup at the level of the carbon dioxide-containing viscous composition at the time of each measurement, removing the composition, pouring water into the cup to the level of the composition and measuring the volume of the water using a graduated cylinder.

TABLE 1

| | Example | 1 | 2 | 3 | 4 | 5 | 6 | 7 | 8 | 9 | 10 | 11 | 12 |
|---|---|---|---|---|---|---|---|---|---|---|---|---|---|
| Carbonate- | <<Carbonate>> | | | | | | | | | | | | |
| containing | Sodium bicarbonate | 2.4 | | 2.4 | | 2.4 | 2.4 | 2.4 | 2.4 | 2.4 | 2.4 | 2.4 | 2.4 |
| aqueous | Sodium carbonate | | 1.2 | | 1.2 | | | | | | | | |

TABLE 1-continued

| | Example | 1 | 2 | 3 | 4 | 5 | 6 | 7 | 8 | 9 | 10 | 11 | 12 |
|---|---|---|---|---|---|---|---|---|---|---|---|---|---|
| viscous | <<Thickener>> | | | | | | | | | | | | |
| composition | Sodium alginate | 4.0 | 4.0 | 3.0 | 3.0 | 3.0 | 3.0 | 3.0 | 3.0 | 3.0 | 3.0 | 3.0 | 3.0 |
| | Ethyl cellulose | | | | | 1.0 | | | | | | | |
| | Carboxyvinyl polymer | | | | | | 1.0 | | | | | | |
| | Carboxymethyl starch sodium | | | | | | | | 2.0 | | | | |
| | Sodium carboxymethylcellulose | | | | | | | | | 2.0 | | | |
| | Xanthan gum | | | | | | | | | | 2.0 | | |
| | Croscarmellose sodium | | | | | | | | | | | 2.0 | |
| | Crystalline cellulose | | | | | | | | | | | 2.0 | |
| | Hydroxypropylcellulose | | | | | | | | | | | | 2.0 |
| | Purified water | 93.6 | 94.8 | 94.6 | 95.8 | 93.6 | 93.6 | 92.6 | 92.6 | 92.6 | 92.6 | 93.6 | 93.6 |
| Acid | Citric acid | 2.0 | | | | 2.0 | 2.0 | 2.0 | 2.0 | 2.0 | 2.0 | 2.0 | 2.0 |
| | Succinic acid | | 1.0 | | | | | | | | | | |
| | Tartaric acid | | | 2.0 | | | | | | | | | |
| | Lactic acid | | | | 1.0 | | | | | | | | |
| Foaming property | | +++ | ++ | +++ | ++ | +++ | +++ | +++ | +++ | +++ | +++ | +++ | +++ |
| Persistence of gas bubbles | | +++ | +++ | ++ | ++ | ++ | +++ | ++ | ++ | +++ | ++ | ++ | ++ |

TABLE 2

| | Example | 13 | 14 | 15 | 16 | 17 | 18 | 19 | 20 | 21 | 22 | 23 | 24 |
|---|---|---|---|---|---|---|---|---|---|---|---|---|---|
| Carbonate- | <<Carbonate>> | | | | | | | | | | | | |
| containing | Sodium bicarbonate | 2.4 | 2.4 | 2.4 | | 2.4 | 2.4 | 2.4 | 2.4 | 2.4 | 2.4 | 2.4 | 2.4 |
| aqueous | Sodium carbonate | | | | 2.4 | | | | | | | | |
| viscous | <<Thickener>> | | | | | | | | | | | | |
| composition | Sodium alginate | 3.0 | 3.0 | 2.0 | 2.0 | 2.0 | 2.0 | 2.0 | 2.0 | 2.0 | 2.0 | 2.0 | 2.0 |
| | Ethyl cellulose | | | | | | | | | | | | |
| | Carboxyvinyl polymer | | | | | 1.0 | | | | | | | |
| | Carboxymethyl starch sodium | | | | | | | 2.0 | 3.0 | 3.0 | 2.0 | 3.0 | 2.0 |
| | Sodium carboxymethylcellulose | | | | | | | 2.0 | 2.0 | 3.0 | 2.0 | 2.0 | 3.0 |
| | Xanthan gum | | | | | | | | | | 1.0 | 1.0 | 1.0 |
| | Croscarmellose sodium | | | | | | | | | | | | 2.0 |
| | Hydroxypropylmethylcellulose | 1.0 | | | | | | | | | | | |
| | Bentonite | | 1.0 | | | | | | | | | | |
| | Polyvinyl alcohol | | | 1.0 | | | | | | | | | |
| | Purified water | 93.6 | 93.6 | 94.6 | 95.6 | 94.6 | 91.6 | 90.6 | 89.6 | 90.6 | 89.6 | 89.6 | 90.6 |
| Acid | Citric acid | 2.0 | 2.0 | 2.0 | 2.0 | 2.0 | 2.0 | 2.0 | 2.0 | 2.0 | 2.0 | 2.0 | 2.0 |
| Foaming property | | +++ | +++ | +++ | +++ | +++ | +++ | +++ | +++ | +++ | +++ | +++ | +++ |
| Persistence of gas bubbles | | ++ | ++ | ++ | + | ++ | ++ | ++ | ++ | ++ | ++ | ++ | ++ |

TABLE 3

| | Example | 25 | 26 | 27 | 28 | 29 | 30 | 31 | 32 | 33 | 34 | 35 | 36 |
|---|---|---|---|---|---|---|---|---|---|---|---|---|---|
| Carbonate- | <<Carbonate>> | | | | | | | | | | | | |
| containing | Sodium bicarbonate | 2.4 | 2.4 | 2.4 | | 2.4 | 2.4 | 2.4 | 2.4 | 2.4 | 2.4 | 2.4 | 2.4 |
| aqueous | Sodium carbonate | | | | 2.4 | | | | | | | | |
| viscous | <<Thickener>> | | | | | | | | | | | | |
| composition | Sodium alginate | 2.0 | 2.0 | 2.0 | 2.0 | 2.0 | 2.0 | 2.0 | 2.0 | 2.0 | 2.0 | 2.0 | 2.0 |
| | Ethyl cellulose | | | | | | | | | | | | |
| | Carboxyvinyl polymer | | | | | | | | | | | | |
| | Carboxymethyl starch sodium | | | | | | | | | | | | |
| | Sodium carboxymethylcellulose | 2.0 | 2.0 | 3.0 | 3.0 | 4.0 | 4.0 | 2.0 | 2.0 | 4.0 | 4.0 | 2.0 | 2.0 |
| | Xanthan gum | 1.0 | 2.0 | 1.0 | 2.0 | 1.0 | 2.0 | | | | | 1.0 | 1.0 |
| | Croscarmellose sodium | | | | | | | 2.0 | 4.0 | 2.0 | 4.0 | 2.0 | 4.0 |
| | Purified water | 92.6 | 91.6 | 91.6 | 90.6 | 90.6 | 89.6 | 91.6 | 89.6 | 89.6 | 87.6 | 90.6 | 88.6 |
| Acid | Citric acid | 2.0 | 2.0 | 2.0 | 2.0 | 2.0 | 2.0 | 2.0 | 2.0 | 2.0 | 2.0 | 2.0 | 2.0 |
| Foaming property | | +++ | +++ | +++ | +++ | +++ | +++ | +++ | +++ | +++ | +++ | +++ | +++ |
| Persistence of gas bubbles | | ++ | +++ | ++ | +++ | ++ | +++ | ++ | ++ | +++ | +++ | +++ | +++ |

TABLE 4

| | Example | 37 | 38 | 39 | 40 | 41 | 42 | 43 | 44 | 45 | 46 | 47 | 48 |
|---|---|---|---|---|---|---|---|---|---|---|---|---|---|
| Carbonate-containing aqueous viscous composition | <<Carbonate>> | | | | | | | | | | | | |
| | Sodium bicarbonate | 2.4 | 2.4 | 2.4 | | 2.4 | 2.4 | 2.4 | 2.4 | 2.4 | 2.4 | 2.4 | 2.4 |
| | Sodium carbonate | | | | 2.4 | | | | | | | | |
| | <<Thickener>> | | | | | | | | | | | | |
| | Sodium alginate | 2.0 | 2.0 | 2.0 | 2.0 | 2.0 | 2.0 | 2.0 | 2.0 | 2.0 | 2.0 | 2.0 | 2.0 |
| | Sodium carboxymethylcellulose | 2.0 | 2.0 | 2.0 | 2.0 | 2.0 | 2.0 | 2.0 | | | | | |
| | Xanthan gum | | 1.0 | 2.0 | | 1.0 | 1.0 | 1.0 | 2.0 | 3.0 | 2.0 | 2.0 | 2.0 |
| | Croscarmellose sodium | | | | 1.0 | | | | | | 2.0 | 4.0 | |
| | Crystalline cellulose | 2.0 | 2.0 | 2.0 | 2.0 | | | | | | | | 2.0 |
| | Hydroxypropylcellulose | | | | | 2.0 | | | | | | | |
| | Hydroxypropylmethylcellulose | | | | | | 2.0 | | | | | | |
| | Bentonite | | | | | | | 2.0 | | | | | |
| | Purified water | 91.6 | 90.6 | 89.6 | 90.6 | 90.6 | 90.6 | 90.6 | 93.6 | 92.6 | 91.6 | 89.6 | 91.6 |
| Acid | Citric acid | 2.0 | 2.0 | 2.0 | 2.0 | 2.0 | 2.0 | 2.0 | 2.0 | 2.0 | 2.0 | 2.0 | 2.0 |
| Foaming property | | +++ | +++ | +++ | +++ | +++ | +++ | +++ | +++ | +++ | +++ | +++ | +++ |
| Persistence of gas bubbles | | ++ | ++ | +++ | ++ | ++ | ++ | ++ | ++ | +++ | +++ | +++ | +++ |

TABLE 5

| | Example | 49 | 50 | 51 | 52 | 53 | 54 | 55 | 56 | 57 | 58 | 59 | 60 |
|---|---|---|---|---|---|---|---|---|---|---|---|---|---|
| Carbonate-containing aqueous viscous composition | <<Carbonate>> | | | | | | | | | | | | |
| | Sodium bicarbonate | 2.4 | 2.4 | 2.4 | | 2.4 | 2.4 | 2.4 | 2.4 | 2.4 | 2.4 | 2.4 | 2.4 |
| | Sodium carbonate | | | | 2.4 | | | | | | | | |
| | <<Thickener>> | | | | | | | | | | | | |
| | Sodium alginate | 2.0 | 2.0 | 2.0 | 2.0 | 2.0 | 2.0 | 2.0 | 2.0 | 2.0 | 2.0 | 2.0 | 2.0 |
| | Xanthan gum | 2.0 | 2.0 | 2.0 | 2.0 | 2.0 | | | | | | | |
| | Croscarmellose sodium | | | | 2.0 | | 2.0 | 3.0 | 4.0 | 4.0 | 4.0 | 4.0 | 4.0 |
| | Crystalline cellulose | | | | 2.0 | 2.0 | | | | 2.0 | | | |
| | Hydroxypropylcellulose | 2.0 | | | | 2.0 | | | | | 2.0 | | |
| | Hydroxypropylmethylcellulose | | 2.0 | | | | | | | | | 2.0 | |
| | Bentonite | | | 2.0 | | | | | | | | | 2.0 |
| | Purified water | 91.6 | 91.6 | 91.6 | 89.6 | 89.6 | 93.6 | 92.6 | 91.6 | 89.6 | 89.6 | 89.6 | 89.6 |
| Acid | Citric acid | 2.0 | 2.0 | 2.0 | 2.0 | 2.0 | 2.0 | 2.0 | 2.0 | 2.0 | 2.0 | 2.0 | 2.0 |
| Foaming property | | +++ | +++ | +++ | +++ | +++ | +++ | +++ | +++ | +++ | +++ | +++ | +++ |
| Persistence of gas bubbles | | +++ | +++ | +++ | +++ | +++ | + | + | ++ | ++ | ++ | ++ | ++ |

TABLE 6

| | Example | 61 | 62 | 63 | 64 | 65 | 66 | 67 | 68 | 69 | 70 | 71 | 72 |
|---|---|---|---|---|---|---|---|---|---|---|---|---|---|
| Carbonate-containing aqueous viscous composition | <<Carbonate>> | | | | | | | | | | | | |
| | Sodium bicarbonate | 2.4 | 2.4 | 2.4 | | 2.4 | 2.4 | 2.4 | 2.4 | 2.4 | 2.4 | 2.4 | 2.4 |
| | Sodium carbonate | | | | 2.4 | | | | | | | | |
| | <<Thickener>> | | | | | | | | | | | | |
| | Sodium alginate | 2.0 | 2.0 | 2.0 | 2.0 | 2.0 | 2.0 | 2.0 | 2.0 | 2.0 | 2.0 | 2.0 | 2.0 |
| | Crystalline cellulose | 2.0 | 4.0 | 4.0 | 4.0 | 4.0 | | | | | | | |
| | Hydroxypropylcellulose | | | 2.0 | | | 2.0 | 4.0 | 4.0 | 4.0 | | | |
| | Hydroxypropylmethylcellulose | | | | 2.0 | | | | 2.0 | | 2.0 | 4.0 | 4.0 |
| | Bentonite | | | | | 2.0 | | | | | | | 2.0 |
| | Purified water | 93.6 | 91.6 | 89.6 | 89.6 | 89.6 | 93.6 | 91.6 | 89.6 | 89.6 | 93.6 | 91.6 | 89.6 |
| Acid | Citric acid | 2.0 | 2.0 | 2.0 | 2.0 | 2.0 | 2.0 | 2.0 | 2.0 | 2.0 | 2.0 | 2.0 | 2.0 |
| Foaming property | | +++ | +++ | +++ | +++ | +++ | +++ | +++ | +++ | +++ | +++ | +++ | +++ |
| Persistence of gas bubbles | | + | + | ++ | ++ | + | + | ++ | +++ | ++ | + | ++ | ++ |

TABLE 7

| | Example | 73 | 74 | 75 | 76 | 77 | 78 | 79 | 80 | 81 | 82 | 83 | 84 |
|---|---|---|---|---|---|---|---|---|---|---|---|---|---|
| Carbonate-containing aqueous | <<Carbonate>> | | | | | | | | | | | | |
| | Sodium bicarbonate | 2.4 | 2.4 | 2.4 | | 2.4 | 2.4 | 2.4 | 2.4 | | 2.4 | | |
| | Sodium carbonate | | | | 2.4 | | | | | 2.4 | | 2.4 | 2.4 |

TABLE 7-continued

|  |  | 73 | 74 | 75 | 76 | 77 | 78 | 79 | 80 | 81 | 82 | 83 | 84 |
|---|---|---|---|---|---|---|---|---|---|---|---|---|---|
| viscous | <<Thickener>> | | | | | | | | | | | | |
| composition | Sodium alginate | 2.0 | 2.0 | 2.0 | 2.0 | 2.0 | 2.0 | 2.0 | | 1.0 | 1.0 | | |
| | Ethyl cellulose | | | | | | | | 2.0 | | | | |
| | Carboxyvinyl polymer | | | | | | | | | | | 1.0 | 1.0 |
| | Carboxymethyl starch sodium | 2.0 | | | | | 2.0 | 2.0 | 2.0 | | | | 2.0 |
| | Sodium carboxymethylcellulose | | 2.0 | | | | 2.0 | 3.0 | 3.0 | 4.0 | | 3.0 | 2.5 |
| | Croscarmellose sodium | | | | 4.0 | | | | | 2.0 | | 2.0 | |
| | Crystalline cellulose | | | 4.0 | | | | | | | 4.0 | | |
| | Bentonite | | | | | 2.0 | | | | | | | |
| | Polyvinyl alcohol | 2.0 | 2.0 | 1.0 | 2.0 | 2.0 | | | | | 1.0 | | |
| | Purified water | 91.6 | 91.6 | 90.6 | 89.6 | 91.6 | 91.6 | 90.6 | 90.6 | 90.6 | 91.6 | 91.6 | 92.1 |
| Acid | Citric acid | 2.0 | 2.0 | 2.0 | 2.0 | 2.0 | | | | | 1.0 | | |
| | Succinic acid | | | | | | 2.0 | | | | | 1.0 | |
| | Tartaric acid | | | | | | | 2.0 | | | 1.0 | | 1.0 |
| | Lactic acid | | | | | | | | 2.0 | | 1.0 | | |
| | Potassium dihydrogenphosphate | | | | | | | | | 2.0 | | | 1.0 |
| Foaming property | | +++ | +++ | +++ | +++ | +++ | +++ | +++ | +++ | ++ | +++ | +++ | +++ |
| Persistence of gas bubbles | | ++ | ++ | ++ | +++ | +++ | ++ | +++ | +++ | +++ | ++ | +++ | +++ |

EXAMPLES 85–108

Tables 8 to 9 show carbon dioxide-containing viscous compositions each prepared by mixing an acid-containing aqueous viscous composition and a carbonate.

Production Process

Acid-containing aqueous viscous compositions are prepared combining thickeners, purified water and acids (organic acids and/or an inorganic acid) as shown in Tables 8 to 9. Carbonates may be used as they are or crystalline salts may be used after being pulverized or dissolved or dispersed in a suitable solvent. The obtained acid-containing aqueous viscous composition and the carbonate are mixed to provide a carbon dioxide-containing viscous composition.

<Preparation of the Acid-containing Aqueous Viscous Compositions>

The thickener or thickeners are dissolved or swollen in purified water in a container such as a beaker, and the acid is dissolved or dispersed. If necessary, the purified water may be heated to promote dissolution or swelling of the thickeners, and the thickeners may be dissolved or dispersed in a suitable solvent before use. If necessary, suitable additives and medicinal substances may also be added.

Evaluation of the Carbon Dioxide-containing Viscous Compositions

<Foaming Property>

50 g of the acid-containing aqueous viscous composition and 1.2 g of the carbonate are placed in a cup 5 cm in diameter and 10 cm high to measure the volume. The mixture is stirred 20 times for 10 seconds to provide a carbon dioxide-containing viscous composition. One minute after stirring, the volume of the composition is measured to determine volume increase % as compared to the volume before stirring. The composition is evaluated for its foaming property according to criteria 1.

The volume is measured in accordance with the method described in Examples 1–84, [Evaluation of the carbon dioxide-containing viscous compositions], <Foaming property>.

<Persistence of Gas Bubbles>

50 g of the acid-containing aqueous viscous composition and 1.2 g of the carbonate are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of gas bubbles is evaluated according to criteria 2.

The volume is measured in accordance with the method described in Examples 1–84, [Evaluation of the carbon dioxide-containing viscous compositions], <Persistence of Gas Bubbles>.

TABLE 8

|  |  | 85 | 86 | 87 | 88 | 89 | 90 | 91 | 92 | 93 | 94 | 95 | 96 |
|---|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| aqueous | Sodium alginate | 4.0 | 4.0 | 4.0 | 3.0 | 3.0 | 3.0 | 3.0 | 2.0 | 2.0 | 2.0 | 2.0 | 2.0 |
| viscous | Ethyl cellulose | | | | | | | | 2.0 | | | | |
| composition | Carboxyvinyl polymer | | | | 1.0 | | | | | 2.0 | 1.0 | | |
| | Carboxymethyl starch sodium | | 2.0 | 2.0 | | 2.0 | 3.0 | | | | 2.0 | 2.0 | |
| | Sodium carboxymethylcellulose | | | 2.0 | | | | | | | | 2.0 | |
| | Xanthan gum | | | | | | | 1.0 | 1.0 | | | | 2.0 |
| | Croscarmellose sodium | | | | | | | | | | | 2.0 | |
| | Crystalline cellulose | | | | | | | | 4.0 | | | | |
| | Purified water | 94.0 | 92.0 | 90.0 | 94.0 | 93.0 | 91.0 | 90.0 | 94.0 | 94.0 | 93.0 | 90.0 | 94.0 |

TABLE 8-continued

| Example | 85 | 86 | 87 | 88 | 89 | 90 | 91 | 92 | 93 | 94 | 95 | 96 |
|---|---|---|---|---|---|---|---|---|---|---|---|---|
| Carbonate  Sodium bicarbonate | 2.4 | 2.4 | 2.4 | 2.4 | 2.4 | 2.4 | 2.4 | 2.4 | 2.4 | 2.4 | 2.4 | 2.4 |
| Foaming property | +++ | +++ | +++ | +++ | +++ | +++ | +++ | +++ | +++ | +++ | +++ | +++ |
| Persistence of gas bubbles | ++ | +++ | +++ | +++ | ++ | +++ | +++ | ++ | +++ | +++ | +++ | +++ |

TABLE 9

| | Example | 97 | 98 | 99 | 100 | 101 | 102 | 103 | 104 | 105 | 106 | 107 | 108 |
|---|---|---|---|---|---|---|---|---|---|---|---|---|---|
| Acid- | <<Acid>> | | | | | | | | | | | | |
| containing | Citric acid | 2.0 | 2.0 | 2.0 | 2.0 | 2.0 | | | | | 1.0 | | |
| aqueous | Succinic acid | | | | | | 2.0 | | | | | 1.0 | |
| viscous | Tartaric acid | | | | | | | 2.0 | | | 1.0 | | 1.0 |
| composition | Lactic acid | | | | | | | | 2.0 | | | | 1.0 |
| | Potassium dihydrogenphosphate | | | | | | | | | 2.0 | | 1.0 | |
| | <<Thickener>> | | | | | | | | | | | | |
| | Sodium alginate | 1.0 | 1.0 | 1.0 | | | 2.0 | | 1.0 | 1.0 | | 3.0 | |
| | Ethyl cellulose | | | | | | | | | | 1.0 | | |
| | Carboxyvinyl polymer | | | | | | | | 1.0 | | 1.0 | | 1.0 |
| | Carboxymethyl starch sodium | | | | | 2.5 | 2.0 | | | | | 1.0 | |
| | Sodium carboxymethylcellulose | 2.0 | 3.0 | | | | | 4.0 | 3.0 | 2.0 | 3.0 | 2.0 | 2.0 |
| | Xanthan gum | 2.0 | 2.0 | | 2.0 | 2.0 | 2.0 | | | 2.0 | | | |
| | Croscarmellose sodium | 2.0 | | | 2.0 | | | 2.0 | | 2.0 | | | |
| | Crystalline cellulose | | | | | | | | | | | | |
| | Hydroxypropylcellulose | | | 2.0 | | 1.0 | | | | | 1.0 | | 1.0 |
| | Hydroxypropylmethylcellulose | | | | | | | | | | | | |
| | Bentonite | | | | | | | | | | | 1.0 | |
| | Polyvinyl alcohol | | 1.0 | 2.0 | | | | | | | | | |
| | Purified water | 91.0 | 91.0 | 93.0 | 94.0 | 95.0 | 91.5 | 90.0 | 93.0 | 91.0 | 92.0 | 91.0 | 94.0 |
| Carbonate | Sodium bicarbonate | 2.4 | 2.4 | 2.4 | 2.4 | 2.4 | | | | | 2.4 | 2.4 | |
| | Sodium carbonate | | | | | | 2.4 | 2.4 | 2.4 | 2.4 | | | 2.4 |
| Foaming property | | +++ | +++ | +++ | +++ | +++ | +++ | +++ | +++ | ++ | +++ | ++ | +++ |
| Persistence of gas bubbles | | +++ | +++ | ++ | +++ | +++ | +++ | +++ | ++ | +++ | +++ | +++ | ++ |

EXAMPLES 109–144

Tables 10 to 12 show carbon dioxide-containing viscous compositions each prepared by mixing a carbonate-containing aqueous viscous composition and a granular acid.

Production Process

Carbonate-containing aqueous viscous compositions and granular acids are prepared combining thickeners, purified water, a carbonate, acids (organic acids and/or an inorganic acid) and matrix bases as shown in Tables 10 to 12. The granular acid may be a sustained release granule. The carbonate-containing aqueous viscous composition and the granular acid are mixed to provide a carbon dioxide-containing viscous composition. The matrix base of the invention may be any compound that is fluidized by dissolution or swelling in a solvent or melting by heating so as to contain other compounds, solidified by removing the solvent or cooling and forms granules by pulverization, etc., or is mixed with other compounds and compressed for solidification and forms granules by pulverization etc., the compound being dissolved or disintegrated in water. Examples of matrix bases are ethyl cellulose, erythritol, carboxymethyl starch and salts thereof, carboxymethylcellulose and salts thereof, silicon dioxide hydrate, xylitol, croscarmellose sodium, light silicic anhydride, crystalline cellulose, synthetic aluminum silicate, synthetic hydrotalcite, stearyl alcohol, cetanol, sorbitol, dextrin, starch, lactose, saccharose, hydroxyethylcellulose, hydroxypropylcellulose, hydroxypropylmethylcellulose, hydroxypropylmethylcellulose acetate succinate, hydroxypropylmethylcellulose phthalate, pullulan, polyethylene glycol, polyvinyl alcohol, polyvinylpyrrolidone, mannose, methylcellulose and the like. The matrix bases can be used singly or in combination of two or more.

<Preparation of the Carbonate-containing Aqueous Viscous Compositions>

The carbonate-containing aqueous viscous compositions are prepared in accordance with the process for preparation of carbonate-containing aqueous viscous compositions as described in Examples 1–84.

<Production of the Granular Acids>

In the case that the matrix base is a low-melting-point compound, the low-melting-point matrix base is melted by heating in a container such as a beaker and then the acid or acids are added and the mixture is fully stirred. If necessary, suitable additives and medicinal substances may be added. The mixture is further stirred while being gradually cooled at room temperature and then allowed to stand until it solidifies. When the mixture solidifies to some extent, it may be quickly cooled using a refrigerator, etc. In the case that the matrix base is not a low-melting-point compound, the matrix base is dissolved or dispersed in a suitable solvent such as water or ethanol in a container such as a beaker, then the acid or acids are dissolved or dispersed therein with fully stirring, and the resulting solution or dispersion is heated using an oven, etc. to remove the solvent and dry the residue. After the residue completely solidifies, the solid is pulverized into granules. To homogenize the size of the granules, the granules may be passed through a filter.

The process for preparing the granular acids according to the present invention is not limited to those described in the Examples. The granular acids may be prepared according to conventional methods, for example, dry crushing, wet crushing, fluidized bed granulation, high-speed stirring granulation, extrusion granulation and like operations.

Evaluation of the Carbon Dioxide-containing Viscous Compositions

<Foaming Property>

50 g of the carbonate-containing aqueous viscous composition and the granular acid containing 1 g of acid are placed in a cup 5 cm in diameter and 10 cm high to measure the volume. The mixture is stirred 20 times for 10 seconds to provide a carbon dioxide-containing viscous composition. One minute after stirring, the volume of the composition is measured to determine volume increase % as compared to the volume before stirring. The composition is evaluated for its foaming property according to criteria 1.

The volume is measured in accordance with the method described in Examples 1–84, [Evaluation of the carbon dioxide-containing viscous compositions], <Foaming property>.

<Persistence of Gas Bubbles>

50 g of the carbonate-containing aqueous viscous composition and the granular acid containing 1 g of acid are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of gas bubbles is evaluated according to criteria 2.

The volume is measured in accordance with the method described in Examples 1–84, [Evaluation of the carbon dioxide-containing viscous compositions], <Persistence of Gas Bubbles>.

TABLE 10

| | Example | 109 | 110 | 111 | 112 | 113 | 114 | 115 | 116 | 117 | 118 | 119 | 120 |
|---|---|---|---|---|---|---|---|---|---|---|---|---|---|
| Carbonate-containing | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| aqueous viscous composition | Sodium alginate | 4.0 | 4.0 | 4.0 | 3.0 | 3.0 | 3.0 | 2.0 | 2.0 | 2.0 | 2.0 | 2.0 | 2.0 |
| | Ethyl cellulose | 2.0 | | | | | | | | | | | |
| | Carboxyvinyl polymer | | 1.0 | | | | 2.0 | | | | | | |
| | Carboxymethyl starch sodium | | | 3.0 | 4.0 | | | 3.0 | | | 3.0 | 3.0 | 3.0 |
| | Sodium carboxymethylcellulose | 2.0 | | | | 2.0 | | | 4.0 | | | | |
| | Xanthan gum | | | 1.0 | 1.0 | | | | | | 2.0 | 2.0 | 2.0 |
| | Croscarmellose sodium | | | | | | | | 2.0 | | | | |
| | Crystalline cellulose | | | | | | | | | 4.0 | | | |
| | Hydroxypropylmethylcellulose | | | | | 2.0 | | | | | | | |
| | Bentonite | | | | | | | | | | 4.0 | | |
| | Polyvinyl alcohol | | | | | | | | | | 2.0 | | |
| | Purified water | 89.6 | 92.6 | 89.6 | 89.6 | 90.6 | 92.6 | 86.6 | 89.6 | 89.6 | 90.6 | 90.6 | 90.6 |
| Granular acid | Citric acid | 2.0 | 2.0 | 2.0 | 2.0 | 2.0 | 2.0 | 2.0 | 2.0 | 2.0 | 2.0 | 2.0 | 2.0 |
| | <<Matrix base>> | | | | | | | | | | | | |
| | Ethyl cellulose | 2.0 | 2.0 | 1.0 | | | | | | | | | |
| | Erythritol | | | | 3.5 | | | | | | | | |
| | Carboxymethyl starch sodium | | | | | 4.0 | | | | | | | |
| | Sodium carboxymethylcellulose | | | | | | | 1.0 | 2.0 | 4.0 | | | |
| | Croscarmellose sodium | 4.0 | 4.0 | 4.0 | 2.5 | | | | | | | | |
| | Stearic acid monoglyceride | | | | | | | | | | 0.5 | 0.02 | 0.05 |
| | Cetanol | | | | | | | | | | 0.2 | 0.5 | 0.5 |
| | Sorbitol | | | | 0.5 | | | | | | | | |
| | Hydroxypropylcellulose | | 0.5 | | | 0.5 | | | | | | | |
| | Hydroxypropylmethylcellulose | | | 0.5 | | | 0.5 | 0.5 | 0.5 | | | | |
| Foaming property | | +++ | +++ | +++ | +++ | +++ | +++ | +++ | ++ | +++ | +++ | +++ | +++ |
| Persistence of gas bubbles | | +++ | +++ | +++ | +++ | ++ | +++ | +++ | +++ | +++ | +++ | +++ | +++ |

TABLE 11

| | Example | 121 | 122 | 123 | 124 | 125 | 126 | 127 | 128 | 129 | 130 | 131 | 132 |
|---|---|---|---|---|---|---|---|---|---|---|---|---|---|
| Carbonate-containing | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| aqueous viscous composition | Sodium alginate | 2.0 | 2.0 | 2.0 | 2.0 | 2.0 | 2.0 | 2.0 | 2.0 | 2.0 | 2.0 | 2.0 | 2.0 |
| | Ethyl cellulose | | | | | | | | | | | | |
| | Carboxyvinyl polymer | | | | | | | | | | | | |
| | Carboxymethyl starch sodium | 3.0 | 3.0 | 3.0 | 3.0 | 3.0 | 3.0 | 3.0 | 3.0 | 3.0 | 3.0 | 3.0 | 3.0 |
| | Sodium carboxymethylcellulose | | | | | | | | | | | | |
| | Xanthan gum | 2.0 | 2.0 | 2.0 | 2.0 | 2.0 | 2.0 | 2.0 | 2.0 | 2.0 | 2.0 | 2.0 | 2.0 |
| | Purified water | 90.6 | 90.6 | 90.6 | 90.6 | 90.6 | 90.6 | 90.6 | 90.6 | 90.6 | 90.6 | 90.6 | 90.6 |
| Granular acid | Citric acid | 2.0 | 2.0 | 2.0 | 2.0 | 2.0 | 2.0 | 2.0 | 2.0 | 2.0 | 2.0 | 2.0 | 2.0 |
| | <<Matrix base>> | | | | | | | | | | | | |
| | Ethyl cellulose | | | | | | | | 6.0 | 2.0 | 2.0 | 1.0 | |
| | Erythritol | | | | | | | | | | | | 3.5 |
| | Xylitol | | | | | | 6.0 | 10.0 | | | | | |
| | Croscarmellose sodium | | | | 5.0 | 5.0 | 5.0 | 5.0 | 4.0 | 4.0 | 4.0 | 2.5 | 5.0 |

TABLE 11-continued

| | Example | 121 | 122 | 123 | 124 | 125 | 126 | 127 | 128 | 129 | 130 | 131 | 132 |
|---|---|---|---|---|---|---|---|---|---|---|---|---|---|
| | Cetanol | 0.5 | 0.2 | 0.1 | | | | | | | | | |
| | Sorbitol | | | | | | | | | | | 0.5 | 6.0 |
| | Hydroxypropylcellulose | 0.05 | | | | | | | | 0.5 | | | |
| | Hydroxypropylmethylcellulose | | | | | | | | | | 0.5 | | |
| Foaming property | | ++ | ++ | ++ | ++ | +++ | +++ | ++ | + | ++ | ++ | +++ | ++ |
| Persistence of gas bubbles | | +++ | +++ | +++ | +++ | +++ | +++ | +++ | +++ | +++ | +++ | +++ | +++ |

TABLE 12

| | | Example | 133 | 134 | 135 | 136 | 137 | 138 | 139 | 140 | 141 | 142 | 143 | 144 |
|---|---|---|---|---|---|---|---|---|---|---|---|---|---|---|
| Carbonate-containing | | Sodium bicarbonate | 2.4 | 2.4 | 2.4 | 2.4 | 2.4 | 2.4 | 2.4 | 2.4 | 2.4 | 2.4 | 2.4 | 2.4 |
| | | <<Thickener>> | | | | | | | | | | | | |
| aqueous | | Sodium alginate | 2.0 | 2.0 | 2.0 | 2.0 | 1.0 | 1.0 | 1.0 | 3.0 | | 2.0 | | |
| viscous | | Carboxyvinyl polymer | | | | | | | | | 1.0 | | 1.0 | |
| composition | | Carboxymethyl starch sodium | 3.0 | 3.0 | 3.0 | 3.0 | 3.0 | 3.0 | 3.0 | 2.0 | 1.0 | | 2.0 | 2.0 |
| | | Sodium carboxymethylcellulose | | 2.0 | 2.0 | 2.0 | 2.0 | 2.0 | 2.0 | 2.0 | | 3.0 | 2.0 | 4.0 |
| | | Xanthan gum | 2.0 | | | | | | | | | | | |
| | | Croscarmellose sodium | | | | | | | | | | 2.0 | | |
| | | Crystalline cellulose | | | | | | | 2.0 | | | | | |
| | | Hydroxypropylcellulose | | | | | | 2.0 | | | | | | |
| | | Hydroxypropylmethylcellulose | | | | | 2.0 | | | | | 2.0 | | |
| | | Bentonite | | | | | | | | | | | | 1.0 |
| | | Polyvinyl alcohol | | | | | | | | | | | 1.0 | |
| | | Purified water | 90.6 | 90.6 | 90.6 | 90.6 | 89.6 | 89.6 | 89.6 | 90.6 | 93.6 | 90.6 | 91.6 | 90.6 |
| Granular | | <<Acid>> | | | | | | | | | | | | |
| acid | | Citric acid | 2.0 | 2.0 | 2.0 | 2.0 | 2.0 | 2.0 | 2.0 | | | | | |
| | | Succinic acid | | | | | | | | 2.0 | | | | |
| | | Tartaric acid | | | | | | | | | | 2.0 | | 1.0 |
| | | Lactic acid | | | | | | | | | | 2.0 | | 1.0 |
| | | Potassium dihydrogenphosphate | | | | | | | | | | | 2.0 | |
| | | <<Matrix base>> | | | | | | | | | | | | |
| | | Ethyl cellulose | | | | 0.5 | 1.0 | 1.0 | 1.0 | | | 1.0 | | |
| | | Erythritol | | | | | | | | | 1.0 | | | |
| | | Carboxymethyl starch sodium | | | | | | | | | | | | 0.5 |
| | | Sodium carboxymethylcellulose | | | | | | | | | 0.5 | | | |
| | | Xylitol | | | | | | | | | | | | 1.0 |
| | | Croscarmellose sodium | 5.0 | 2.0 | 2.0 | 2.0 | 2.0 | 2.0 | 2.0 | 2.0 | | 2.0 | 2.0 | |
| | | Stearic acid monoglyceride | | | | | | | | | 0.5 | | | |
| | | Cetanol | | | | | | | | | | | 1.0 | |
| | | Hydroxypropylcellulose | | | 0.5 | 0.25 | 0.25 | | | 0.5 | | 0.25 | | |
| | | Hydroxypropylmethylcellulose | | 1.5 | | | | | | | | | | |
| | | Mannose | 6.0 | | | | | | | | | | | |
| Foaming property | | | ++ | +++ | +++ | +++ | +++ | +++ | +++ | +++ | +++ | +++ | ++ | +++ |
| Persistence of gas bubbles | | | +++ | ++ | ++ | ++ | +++ | +++ | +++ | +++ | ++ | +++ | +++ | +++ |

EXAMPLES 145–179

Tables 13 to 15 show carbon dioxide-containing viscous compositions each prepared by mixing an acid-containing aqueous viscous composition and a granular carbonate.

Production Process

Acid-containing aqueous viscous compositions and granular carbonates are prepared combining thickeners, purified water, a carbonate, acids (organic acids and/or an inorganic acid) and matrix bases as shown in Tables 13 to 15. The granular carbonate may be a sustained release granule. The obtained acid-containing aqueous viscous composition and the granular carbonate are mixed to provide a carbon dioxide-containing viscous composition. <Preparation of the Acid-containing Aqueous Viscous Compositions>

The acid-containing aqueous viscous compositions are prepared in accordance with the process for preparation of acid-containing aqueous viscous compositions as described in Examples 85–108.

<Preparation of the Granular Carbonates>

In the case that the matrix base is a low-melting-point compound, the low-melting-point matrix base is melted by heating in a container such as a beaker and then the carbonate is added and the mixture is fully stirred. If necessary, suitable additives and medicinal substances may be added. The mixture is further stirred while being gradually cooled at room temperature and then allowed to stand until it solidifies. When the mixture solidifies to some extent, it may be quickly cooled using a refrigerator, etc. In the case that the matrix base is not a low-melting-point compound, the matrix base is dissolved or dispersed in a suitable solvent such as water or ethanol in a container such as a beaker, then the carbonate is dissolved or dispersed therein with fully stirring, and the resulting solution or dispersion is heated using an oven, etc. to remove the solvent and dry the residue. After the residue completely solidifies, the solid is pulverized into granules. To homogenize the size of the granules, the granules may be passed through a filter.

The process for preparing the granular carbonates according to the present invention is not limited to those described in the Examples. The granular carbonates may be prepared according to conventional methods, for example, dry crushing, wet crushing, fluidized bed granulation, high-speed stirring granulation, extrusion granulation and like operations.

Evaluation of the Carbon Dioxide-containing Viscous Compositions

<Foaming Property>

50 g of the acid-containing aqueous viscous composition and the granular carbonate containing 1.2 g of carbonate are placed in a cup 5 cm in diameter and 10 cm high to measure the volume. The mixture is stirred 20 times for 10 seconds to provide a carbon dioxide-containing viscous composition. One minute after stirring, the volume of the composition is measured to determine volume increase % as compared to the volume before stirring. The composition is evaluated for its foaming property according to criteria 1.

The volume is measured in accordance with the method described in Examples 1–84, [Evaluation of the carbon dioxide-containing viscous compositions], <Foaming property>.

<Persistence of Gas Bubbles>

50 g of the acid-containing aqueous viscous composition and the granular carbonate containing 1.2 g of carbonate are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of gas bubbles is evaluated according to criteria 2.

The volume is measured in accordance with the method described in Examples 1–84, [Evaluation of the carbon dioxide-containing viscous compositions], <Persistence of gas bubbles>.

TABLE 13

| | Example | 145 | 146 | 147 | 148 | 149 | 150 | 151 | 152 | 153 | 154 | 155 | 156 |
|---|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| aqueous viscous composition | Sodium alginate | 4.0 | 4.0 | 4.0 | 3.0 | 3.0 | 3.0 | 2.0 | 2.0 | 2.0 | 2.0 | 2.0 | 2.0 |
| | Ethyl cellulose | 2.0 | | | | | | | | | | | |
| | Carboxyvinyl polymer | | 1.0 | | | | 2.0 | | | | | | |
| | Carboxymethyl starch sodium | | | 3.0 | 4.0 | | | 3.0 | | | 3.0 | 3.0 | 3.0 |
| | Sodium carboxymethylcellulose | 2.0 | | | | 2.0 | | 4.0 | | | | | |
| | Xanthan gum | | | 1.0 | 1.0 | | | | | | 2.0 | 2.0 | 2.0 |
| | Croscarmellose sodium | | | | | | | | 2.0 | | | | |
| | Crystalline cellulose | | | | | | | | | | 4.0 | | |
| | Hydroxypropylmethylcellulose | | | | | 2.0 | | | | | | | |
| | Bentonite | | | | | | | | | 4.0 | | | |
| | Polyvinyl alcohol | | | | | | | | | 2.0 | | | |
| | Purified water | 90.0 | 93.0 | 90.0 | 90.0 | 91.0 | 93.0 | 87.0 | 90.0 | 90.0 | 91.0 | 91.0 | 91.0 |
| Granular carbonate | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Matrix base>> | | | | | | | | | | | | |
| | Ethyl cellulose | 2.0 | 2.0 | 1.0 | | | | | | | | | |
| | Erythritol | | | | 3.5 | | | | | | | | |
| | Carboxymethyl starch sodium | | | | | 4.0 | | | | | | | |
| | Sodium carboxymethylcellulose | | | | | | 1.0 | 2.0 | 4.0 | | | | |
| | Croscarmellose sodium | 4.0 | 4.0 | 4.0 | 2.5 | | | | | | | | |
| | Stearic acid monoglyceride | | | | | | | | | 0.5 | 0.02 | 0.05 | |
| | Cetanol | | | | | | | | | 0.2 | 0.5 | | 0.5 |
| | Sorbitol | | | | 0.5 | | | | | | | | |
| | Hydroxypropylcellulose | | 0.5 | | | 0.5 | | | | | | | |
| | Hydroxypropylmethylcellulose | | | 0.5 | | | 0.5 | 0.5 | 0.5 | | | | |
| Foaming property | | +++ | +++ | +++ | +++ | +++ | +++ | +++ | ++ | +++ | +++ | +++ | +++ |
| Persistence of gas bubbles | | +++ | +++ | +++ | +++ | ++ | +++ | +++ | +++ | +++ | +++ | +++ | +++ |

TABLE 14

| | Example | 157 | 158 | 159 | 160 | 161 | 162 | 163 | 164 | 165 | 166 | 167 | 168 |
|---|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| aqueous viscous composition | Sodium alginate | 2.0 | 2.0 | 2.0 | 2.0 | 2.0 | 2.0 | 2.0 | 2.0 | 2.0 | 2.0 | 2.0 | 2.0 |
| | Carboxymethyl starch sodium | 3.0 | 3.0 | 3.0 | 3.0 | 3.0 | 3.0 | 3.0 | 3.0 | 3.0 | 3.0 | 3.0 | 3.0 |
| | Xanthan gum | 2.0 | 2.0 | 2.0 | 2.0 | 2.0 | 2.0 | 2.0 | 2.0 | 2.0 | 2.0 | 2.0 | 2.0 |
| | Purified water | 91.0 | 91.0 | 91.0 | 91.0 | 91.0 | 91.0 | 91.0 | 91.0 | 91.0 | 91.0 | 91.0 | 91.0 |
| Granular carbonate | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Matrix base>> | | | | | | | | | | | | |
| | Ethyl cellulose | | | | | | | | 6.0 | 2.0 | 2.0 | 1.0 | |
| | Xylitol | | | | | 6.0 | 10.0 | | | | | | |
| | Croscarmellose sodium | | | | 5.0 | 5.0 | 5.0 | 5.0 | 4.0 | 4.0 | 4.0 | 2.5 | 5.0 |
| | Cetanol | 0.5 | 0.2 | 0.1 | | | | | | | | | |

TABLE 14-continued

| Example | | 157 | 158 | 159 | 160 | 161 | 162 | 163 | 164 | 165 | 166 | 167 | 168 |
|---|---|---|---|---|---|---|---|---|---|---|---|---|---|
| | Sorbitol | | | | | | | | | | | 0.5 | 6.0 |
| | Hydroxypropylcellulose | 0.05 | | | | | | | | 0.5 | | | |
| | Hydroxypropylmethylcellulose | | | | | | | | | | 0.5 | | |
| Foaming property | | ++ | ++ | ++ | ++ | +++ | +++ | ++ | + | ++ | ++ | +++ | ++ |
| Persistence of gas bubbles | | +++ | +++ | +++ | +++ | +++ | +++ | +++ | +++ | +++ | +++ | +++ | +++ |

TABLE 15

| | Example | 169 | 170 | 171 | 172 | 173 | 174 | 175 | 176 | 177 | 178 | 179 |
|---|---|---|---|---|---|---|---|---|---|---|---|---|
| Acid- | <<Acid>> | | | | | | | | | | | |
| containing | Citric acid | 2.0 | 2.0 | 2.0 | 2.0 | 2.0 | 2.0 | 2.0 | | | | |
| aqueous | Succinic acid | | | | | | | | 2.0 | | | |
| viscous | Tartaric acid | | | | | | | | | 2.0 | | |
| composition | Lactic acid | | | | | | | | | | 2.0 | |
| | Potassium dihydrogenphosphate | | | | | | | | | | | 2.0 |
| | <<Thickener>> | | | | | | | | | | | |
| | Sodium alginate | 2.0 | 2.0 | 2.0 | 2.0 | 1.0 | 1.0 | 1.0 | | 2.0 | | |
| | Ethyl cellulose | | | | | | | | | 1.0 | | |
| | Carboxyvinyl polymer | | | | | | | | 1.0 | | 1.0 | |
| | Carboxymethyl starch sodium | 3.0 | 3.0 | 3.0 | 3.0 | 3.0 | 3.0 | 3.0 | 2.0 | | | |
| | Sodium carboxymethylcellulose | | 2.0 | 2.0 | 2.0 | 2.0 | 2.0 | 2.0 | 2.0 | | | 4.0 |
| | Xanthan gum | 2.0 | | | | | | | | | 1.0 | |
| | Croscarmellose sodium | | | | | | | | | 2.0 | 3.0 | 2.0 |
| | Crystalline cellulose | | | | | | | | 2.0 | | | |
| | Hydroxypropylcellulose | | | | | | 2.0 | | | | | |
| | Hydroxypropylmethylcellulose | | | | | 2.0 | | | | | | 1.0 |
| | Bentonite | | | | | | | | | | 1.0 | |
| | Polyvinyl alcohol | | | | | | | | | 1.0 | | |
| | Purified water | 91.0 | 91.0 | 91.0 | 91.0 | 90.0 | 90.0 | 90.0 | 93.0 | 92.0 | 92.0 | 91.0 |
| Granular | Sodium bicarbonate | 2.4 | 2.4 | 2.4 | 2.4 | 2.4 | 2.4 | 2.4 | 2.4 | 2.4 | 2.4 | 2.4 |
| carbonate | <<Matrix base>> | | | | | | | | | | | |
| | Ethyl cellulose | | | | 0.5 | 1.0 | 1.0 | 1.0 | | | | |
| | Erythritol | | | | | | | | 1.0 | | | |
| | Xylitol | | | | | | | | | | 1.0 | |
| | Croscarmellose sodium | 5.0 | 2.0 | 2.0 | 2.0 | 2.0 | 2.0 | 2.0 | | | | |
| | Stearic acid monoglyceride | | | | | | | | | | | |
| | Cetanol | | | | | | | | | 1.0 | | |
| | Sorbitol | | | | | | | | | | | 1.0 |
| | Hydroxypropylcellulose | | | 0.5 | 0.25 | 0.25 | | | | 0.25 | | |
| | Hydroxypropylmethylcellulose | | 1.5 | | | | | | 1.0 | | | |
| | Mannose | 6.0 | | | | | | | | | | |
| Foaming property | | ++ | +++ | +++ | +++ | +++ | +++ | +++ | +++ | +++ | +++ | ++ |
| Persistence of gas bubbles | | +++ | ++ | ++ | ++ | +++ | +++ | +++ | ++ | +++ | +++ | +++ |

EXAMPLES 180–226

Tables 16 to 19 show carbon dioxide-containing iscous compositions each prepared by mixing an acid-containing viscous composition and a carbonate-containing aqueous viscous composition.

Production Process

Acid-containing aqueous viscous compositions and carbonate-containing aqueous viscous compositions are prepared combining thickeners, purified water, carbonates and acids (organic acids and/or an inorganic acid) as shown in Tables 16 to 19. The acid-containing aqueous viscous composition and the carbonate-containing aqueous viscous composition are mixed to provide a carbon dioxide-containing viscous composition.

<Preparation of the Acid-containing Aqueous Viscous Compositions>

The acid-containing aqueous viscous compositions are prepared in accordance with the process for preparation of acid-containing aqueous viscous compositions as described in Examples 85–108.

<Preparation of the Carbonate-containing Aqueous Viscous Compositions>

The carbonate-containing aqueous viscous compositions are prepared in accordance with the process for preparation of carbonate-containing aqueous viscous compositions as described in Examples 1–84.

Evaluation of the Carbon Dioxide-containing Viscous Compositions

<Foaming Property>

25 g of the acid-containing aqueous viscous composition and 25 g of the carbonate-containing aqueous viscous composition are placed in a cup 5 cm in diameter and 10 cm high to measure the volume. The mixture is stirred 20 times for 10 seconds to provide a carbon dioxide-containing viscous composition. One minute after stirring, the volume of the composition is measured to determine volume increase % as compared to the volume before stirring. The composition is evaluated for its foaming property according to criteria 1.

The volume is measured in accordance with the method described in Examples 1–84, [Evaluation of the carbon dioxide-containing viscous compositions], <Foaming property>.

<Persistence of Bubbles>

25 g of the acid-containing aqueous viscous aqueous composition and 25 g of the carbonate-containing aqueous viscous composition are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of bubbles is evaluated according to criteria 2.

The volume is measured in accordance with the method described in Examples 1–84, [Evaluation of the carbon dioxide-containing viscous compositions], <Persistence of gas bubbles>.

TABLE 16

| | Example | 180 | 181 | 182 | 183 | 184 | 185 | 186 | 187 | 188 | 189 | 190 | 191 |
|---|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| aqueous viscous composition | Sodium alginate | 4.0 | 4.0 | 4.0 | 3.0 | 3.0 | 3.0 | 2.0 | 2.0 | 2.0 | 2.0 | 2.0 | 2.0 |
| | Carboxyvinyl polymer | | | | | | 2.0 | | | | | | |
| | Carboxymethyl starch sodium | | | 1.0 | 2.0 | | | 3.0 | | | 2.0 | 3.0 | |
| | Sodium carboxymethylcellulose | | 1.0 | | | 2.0 | | 4.0 | | | 2.0 | | 3.0 |
| | Xanthan gum | | | 1.0 | 1.0 | | | | | 2.0 | | 2.0 | 2.0 |
| | Croscarmellose sodium | | | | | | | 2.0 | | | | | |
| | Crystalline cellulose | | | | | | | | | 4.0 | | | |
| | Hydroxypropylmethylcellulose | | | | | 2.0 | | | | | | | |
| | Bentonite | | | | | | | | 4.0 | | | | |
| | Polyvinyl alcohol | | | | | | | | 2.0 | | | | |
| | Purified water | 94.0 | 93.0 | 92.0 | 92.0 | 91.0 | 93.0 | 87.0 | 90.0 | 92.0 | 91.0 | 91.0 | 91.0 |
| Carbonate-containing | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| aqueous viscous composition | Sodium alginate | 4.0 | 4.0 | 4.0 | 3.0 | 3.0 | 3.0 | 2.0 | 2.0 | 2.0 | 2.0 | 2.0 | 2.0 |
| | Carboxyvinyl polymer | | | | | | 2.0 | | | | | | |
| | Carboxymethyl starch sodium | | | 1.0 | 2.0 | | | 3.0 | | | 2.0 | 3.0 | |
| | Sodium carboxymethylcellulose | | 1.0 | | | 2.0 | | 4.0 | | | 2.0 | | 3.0 |
| | Xanthan gum | | | 1.0 | 1.0 | | | | | 2.0 | | 2.0 | 2.0 |
| | Croscarmellose sodium | | | | | | | 2.0 | | | | | |
| | Crystalline cellulose | | | | | | | | | 4.0 | | | |
| | Hydroxypropylmethylcellulose | | | | | 2.0 | | | | | | | |
| | Bentonite | | | | | | | | 4.0 | | | | |
| | Polyvinyl alcohol | | | | | | | | 2.0 | | | | |
| | Purified water | 93.6 | 92.6 | 91.6 | 91.6 | 90.6 | 92.6 | 86.6 | 89.0 | 89.6 | 91.6 | 91.0 | 91.0 |
| Foaming property | | +++ | +++ | +++ | +++ | +++ | +++ | +++ | +++ | +++ | +++ | +++ | +++ |
| Persistence of gas bubbles | | +++ | +++ | +++ | +++ | +++ | +++ | +++ | ++ | +++ | ++ | +++ | +++ |

TABLE 17

| | Example | 192 | 193 | 194 | 195 | 196 | 197 | 198 | 199 | 200 | 201 | 202 | 203 |
|---|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| aqueous viscous composition | Sodium alginate | 2.0 | 2.0 | 3.0 | 2.0 | 2.0 | | | 1.0 | 1.0 | 1.0 | | |
| | Ethyl cellulose | | | | | | | 2.0 | | | | 3.0 | |
| | Carboxyvinyl polymer | | | | 2.0 | | | | | | | | 2.0 |
| | Carboxymethyl starch sodium | 4.0 | 3.0 | 2.0 | 2.0 | 2.0 | 3.0 | | 2.0 | | 3.0 | | 3.0 |
| | Sodium carboxymethylcellulose | | 2.0 | 2.0 | | | | | 3.0 | 2.0 | | | 2.0 |
| | Xanthan gum | | | | | | 2.0 | 2.0 | | | 2.0 | | |
| | Hydroxypropylcellulose | | | | | 2.0 | | | | | | 2.0 | |
| | Hydroxypropylmethylcellulose | | | | | | | 2.0 | | | | | 2.0 |
| | Polyvinyl alcohol | 2.0 | | | | | | | | | | | |
| | Purified water | 90.0 | 91.0 | 91.0 | 92.0 | 92.0 | 91.0 | 91.0 | 93.0 | 93.0 | 92.0 | 93.0 | 91.0 |
| Carbonate-containing | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| aqueous viscous composition | Sodium alginate | 2.0 | 2.0 | 2.0 | 2.0 | | | | 1.0 | 1.0 | 1.0 | | |
| | Ethyl cellulose | | | | | | | 2.0 | | | | 3.0 | |
| | Carboxyvinyl polymer | | | | | | | | | | | | 2.0 |
| | Carboxymethyl starch sodium | 4.0 | 3.0 | 3.0 | | 3.0 | 3.0 | | 2.0 | | 3.0 | | 3.0 |
| | Sodium carboxymethylcellulose | | 2.0 | | | 2.0 | | 3.0 | 2.0 | 2.0 | | | 2.0 |
| | Xanthan gum | | | 2.0 | 1.0 | 2.0 | 2.0 | 2.0 | | 2.0 | | | |
| | Crystalline cellulose | | | | 3.0 | | | | | | | | |
| | Hydroxypropylcellulose | | | | | | 2.0 | | | | 2.0 | | |
| | Hydroxypropylmethylcellulose | | | | | | | | | | | 2.0 | |
| | Polyvinyl alcohol | 2.0 | | | | | | | | | | | |
| | Purified water | 89.6 | 90.6 | 90.6 | 91.6 | 90.6 | 90.6 | 90.6 | 92.6 | 92.6 | 91.0 | 92.6 | 90.6 |
| Foaming property | | +++ | +++ | +++ | +++ | +++ | +++ | +++ | +++ | +++ | +++ | +++ | +++ |
| Persistence of gas bubbles | | +++ | +++ | +++ | +++ | +++ | +++ | +++ | ++ | +++ | +++ | ++ | +++ |

TABLE 18

| | Example | 204 | 205 | 206 | 207 | 208 | 209 | 210 | 211 | 212 | 213 | 214 | 215 |
|---|---|---|---|---|---|---|---|---|---|---|---|---|---|
| Acid-containing aqueous viscous composition | Citric acid | 2.0 | 2.0 | 2.0 | 2.0 | 2.0 | 2.0 | 2.0 | 2.0 | 2.0 | 2.0 | 2.0 | 2.0 |
| | <<Thickener>> | | | | | | | | | | | | |
| | Sodium alginate | 2.0 | 2.0 | 3.0 | 1.0 | 1.0 | | | | | | | |
| | Ethyl cellulose | | | | | | | | | | | 3.0 | |
| | Carboxyvinyl polymer | | | | | | | | | | 1.0 | | 2.0 |
| | Carboxymethyl starch sodium | 2.0 | 2.0 | 2.0 | 2.0 | 2.0 | 3.0 | | 3.0 | 1.0 | 3.0 | | |
| | Sodium carboxymethylcellulose | 2.0 | 2.0 | 2.0 | 2.0 | 2.0 | | 3.0 | 1.0 | 2.0 | | | 2.0 |
| | Xanthan gum | | | | | 2.0 | 2.0 | 2.0 | 1.0 | | | | 1.0 |
| | Croscarmellose sodium | 2.0 | 2.0 | | | | | | | | | | |
| | Crystalline cellulose | | | | | | | 2.0 | | | | | |
| | Hydroxypropylcellulose | | | | | | 2.0 | | | | | 2.0 | |
| | Hydroxypropylmethylcellulose | | | | | | | | | 2.0 | | 2.0 | |
| | Bentonite | | | | | | | | | | | | 3.0 |
| | Purified water | 90.0 | 90.0 | 91.0 | 93.0 | 91.0 | 91.0 | 91.0 | 93.0 | 93.0 | 92.0 | 93.0 | 90.0 |
| Carbonate-containing aqueous viscous composition | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| | Sodium alginate | 2.0 | 1.0 | 1.0 | 1.0 | 1.0 | | | | | | | |
| | Ethyl cellulose | | | | | | | | | | | 3.0 | |
| | Carboxyvinyl polymer | | | | | | | | | | 1.0 | | 2.0 |
| | Carboxymethyl starch sodium | 2.0 | 2.0 | 2.0 | 2.0 | 2.0 | 3.0 | | 3.0 | 1.0 | 3.0 | | |
| | Sodium carboxymethylcellulose | 2.0 | 2.0 | 2.0 | 2.0 | 2.0 | | 3.0 | 1.0 | 2.0 | | | 2.0 |
| | Xanthan gum | | | | | 2.0 | 2.0 | 2.0 | 1.0 | | | | 1.0 |
| | Croscarmellose sodium | 2.0 | 2.0 | 2.0 | | | | | | | | | |
| | Crystalline cellulose | | | | | | | 2.0 | | | | | |
| | Hydroxypropylcellulose | | | | | | 2.0 | | | | | 2.0 | |
| | Hydroxypropylmethylcellulose | | | | | | | | | 2.0 | | 2.0 | |
| | Bentonite | | | | | | | | | | | | 3.0 |
| | Purified water | 89.6 | 90.6 | 90.6 | 92.6 | 90.6 | 90.6 | 90.6 | 92.6 | 92.6 | 91.6 | 92.6 | 89.6 |
| Foaming property | | +++ | +++ | +++ | +++ | +++ | +++ | +++ | +++ | +++ | +++ | +++ | +++ |
| Persistence of gas bubbles | | +++ | ++ | +++ | + | +++ | +++ | +++ | ++ | +++ | +++ | ++ | +++ |

TABLE 19

| | Example | 216 | 217 | 218 | 219 | 220 | 221 | 222 | 223 | 224 | 225 | 226 |
|---|---|---|---|---|---|---|---|---|---|---|---|---|
| Acid-containing aqueous viscous composition | <<Acid>> | | | | | | | | | | | |
| | Citric acid | | | | | 2.0 | | | | | 1.0 | |
| | Succinic acid | 2.0 | | | | | 2.0 | | | | 1.0 | |
| | Tartaric acid | | 2.0 | | | | | 2.0 | | | | 1.0 |
| | Lactic acid | | | 2.0 | | | | | 2.0 | | | 1.0 |
| | Potassium dihydrogenphosphate | | | | 2.0 | | | | | 2.0 | | |
| | <<Thickener>> | | | | | | | | | | | |
| | Sodium alginate | 2.0 | 2.0 | 2.0 | 2.0 | | | | | | | |
| | Ethyl cellulose | | | | | | | | | | | 3.0 |
| | Carboxyvinyl polymer | | | | | 1.0 | 1.0 | 1.0 | 1.0 | 1.0 | 1.0 | |
| | Carboxymethyl starch sodium | 2.0 | 2.0 | 2.0 | 2.0 | | | | | | 3.0 | |
| | Sodium carboxymethylcellulose | 2.0 | 2.0 | 2.0 | 2.0 | 3.0 | 3.0 | 3.0 | 3.0 | 3.0 | | |
| | Xanthan gum | | | | | | | | | | | 1.0 |
| | Croscarmellose sodium | | | | | 2.0 | 2.0 | 2.0 | 2.0 | 2.0 | | |
| | Crystalline cellulose | | | | | | | | | | 2.0 | |
| | Hydroxypropylmethylcellulose | | | | | | | | | | | 2.0 |
| | Purified water | 92.0 | 92.0 | 92.0 | 92.0 | 92.0 | 92.0 | 92.0 | 92.0 | 92.0 | 92.0 | 93.0 |
| Carbonate-containing aqueous viscous composition | <<Carbonate>> | | | | | | | | | | | |
| | Sodium bicarbonate | 2.4 | 2.4 | 2.4 | 2.4 | | | | | | 2.4 | |
| | Sodium carbonate | | | | | 2.4 | 2.4 | 2.4 | 2.4 | 2.4 | | 2.4 |
| | <<Thickener>> | | | | | | | | | | | |
| | Sodium alginate | 2.0 | 2.0 | 2.0 | 2.0 | | | | | | | |
| | Ethyl cellulose | | | | | | | | | | | 3.0 |
| | Carboxyvinyl polymer | | | | | 1.0 | 1.0 | 1.0 | 1.0 | 1.0 | 1.0 | |
| | Carboxymethyl starch sodium | 2.0 | 2.0 | 2.0 | 2.0 | | | | | | 3.0 | |
| | Sodium carboxymethylcellulose | 2.0 | 2.0 | 2.0 | 2.0 | 3.0 | 3.0 | 3.0 | 3.0 | 3.0 | | |

TABLE 19-continued

| Example | | 216 | 217 | 218 | 219 | 220 | 221 | 222 | 223 | 224 | 225 | 226 |
|---|---|---|---|---|---|---|---|---|---|---|---|---|
| | Xanthan gum | | | | | | | | | | | 1.0 |
| | Croscarmellose sodium | | | | 2.0 | 2.0 | 2.0 | 2.0 | 2.0 | | | |
| | Crystalline cellulose | | | | | | | | | | 2.0 | |
| | Hydroxypropylmethylcellulose | | | | | | | | | | | 2.0 |
| | Purified water | 91.6 | 91.6 | 91.6 | 91.6 | 91.6 | 91.6 | 91.6 | 91.6 | 91.6 | 91.6 | 91.6 |
| Foaming property | | +++ | +++ | +++ | ++ | +++ | +++ | +++ | +++ | ++ | +++ | +++ |
| Persistence of gas bubbles | | +++ | +++ | +++ | +++ | +++ | +++ | +++ | +++ | +++ | +++ | ++ |

EXAMPLES 227–249

Tables 20 and 21 show carbon dioxide-containing viscous compositions each prepared by mixing a composite granule of carbonate and acid and an aqueous viscous composition.

Production Process

Composite granules of carbonate and acid, and aqueous viscous compositions are prepared combining thickeners, purified water, carbonates, acids (organic acids and/or an inorganic acid) and matrix bases as shown in Tables 20 and 21. The composite granule of carbonate and acid and the aqueous viscous composition are mixed to provide a carbon dioxide-containing viscous composition. The composite granule of carbonate and acid may be a controlled release granule permitting sustained release of carbonate and acid.

<Preparation of the Composite Granules of Carbonate and Acid>

In the case that the matrix base is a low-melting-point compound, the low-melting-point matrix base is melted by heating in a container such as a beaker, then the carbonate and the acid are added and the mixture is fully stirred. If necessary, suitable additives and medicinal substances may be added. The mixture is further stirred while being gradually cooled at room temperature and then allowed to stand until it solidifies. When the mixture solidifies to some extent, it may be quickly cooled using a refrigerator, etc. In the case that the matrix base is not a low-melting-point compound, the matrix base is dissolved or dispersed in a suitable solvent such as anhydrous ethanol in a container such as a beaker, then the carbonate and the acid are dissolved or dispersed therein with fully stirring, and the resulting solution or dispersion is heated using an oven, etc. to remove the solvent and dry the residue. When the residue completely solidifies, the solid is pulverized into granules. To homogenize the size of the granules, the granules may be passed through a filter.

<Preparation of the Aqueous Viscous Compositions>

The thickener or thickeners are dissolved or swollen in purified water in a container such as a beaker. If necessary, the purified water may be heated to promote dissolution or swelling of the thickeners, and the thickeners may be dissolved or dispersed in a suitable solvent before use. If necessary, suitable additives and medicinal substances may also be added.

The method for preparing the composite granules of carbonate and acid according to the present invention is not limited to those described in the Examples. The granules may be prepared according to conventional methods, for example, dry crushing, wet crushing, fluidized bed granulation, high-speed stirring granulation, extrusion granulation and like operations.

Evaluation of the Carbon Dioxide-containing Viscous Compositions

<Foaming Property>

50 g of the aqueous viscous composition, and the composite granule of carbonate and acid containing 1.2 g of carbonate are placed in a cup 5 cm in diameter and 10 cm high to measure the volume. The mixture of the aqueous viscous composition and the composite granule are stirred 20 times for 10 seconds to provide a carbon dioxide-containing viscous composition. One minute after stirring, the volume of the composition is measured to determine volume increase % as compared with the volume before stirring. The composition is evaluated for its foaming property according to criteria 1.

The volume is measured in accordance with the method described in Examples 1–84, [Evaluation of carbon dioxide-containing viscous compositions], <Foaming property>.

<Persistence of Gas Bubbles>

50 g of the aqueous viscous composition and the composite granule of carbonate and acid containing 1.2 g of carbonate are placed in a cup 5 cm in diameter and 10 cm high. The mixture is stirred 20 times for 10 seconds to provide a carbon dioxide-containing viscous composition. One minute after stirring, the volume of the composition is measured. Two hours later, the volume is measured again to determine volume decrease %. The persistence of gas bubbles is evaluated according to criteria 2.

The volume is measured in accordance with the method described in Examples 1–84, [Evaluation of carbon dioxide-containing viscous compositions], <Persistence of gas bubbles>.

TABLE 20

| | Example | 227 | 228 | 229 | 230 | 231 | 232 | 233 | 234 | 235 | 236 | 237 | 238 |
|---|---|---|---|---|---|---|---|---|---|---|---|---|---|
| Composite granule of carbonate and acid | Sodium bicarbonate | 2.4 | 2.4 | 2.4 | 2.4 | 2.4 | 2.4 | 2.4 | 2.4 | 2.4 | 2.4 | 2.4 | 2.4 |
| | Citric acid | 2.0 | 2.0 | 2.0 | 2.0 | 2.0 | 2.0 | 2.0 | 2.0 | 2.0 | 2.0 | 2.0 | 2.0 |
| | <<Matrix base>> | | | | | | | | | | | | |
| | Ethyl cellulose | 1.0 | | | | | | | | | | | |
| | Erythritol | | | 2.0 | | | | | | | 2.0 | | |
| | Carboxymethyl starch sodium | | | | | 1.0 | | | | | | | |
| | Sodium carboxymethylcellulose | | | | | | 1.0 | | | | | | |
| | Xylitol | | | | | | | | | 4.0 | | | 2.0 |

TABLE 20-continued

| | Example | 227 | 228 | 229 | 230 | 231 | 232 | 233 | 234 | 235 | 236 | 237 | 238 |
|---|---|---|---|---|---|---|---|---|---|---|---|---|---|
| | Croscarmellose sodium | 2.0 | 2.0 | 1.0 | | | | | | | | | |
| | Stearic acid monoglyceride | 2.0 | | | 0.5 | | | | 0.02 | | | | |
| | Cetanol | | 1.0 | | | | | 0.5 | 0.2 | 0.5 | | | |
| | Hydroxypropylcellulose | | 0.5 | | | 0.5 | | | | | | 0.5 | |
| | Hydroxypropylmethylcellulose | | | 0.5 | | | 0.5 | | | | 0.5 | | 0.5 |
| | Mannose | | | | | | | | | | | 2.0 | |
| Aqueous | <<Thickener>> | | | | | | | | | | | | |
| viscous | Sodium alginate | 4.0 | 4.0 | 3.0 | 3.0 | 3.0 | 3.0 | 2.0 | 2.0 | 3.0 | 3.0 | 3.0 | 3.0 |
| composition | Carboxyvinyl polymer | | 1.0 | | | | 2.0 | | | | | | 2.0 |
| | Carboxymethyl starch sodium | | | 3.0 | 4.0 | | | | 3.0 | 3.0 | 4.0 | | |
| | Sodium carboxymethylcellulose | | | | | 2.0 | | 2.0 | | | | 2.0 | |
| | Xanthan gum | | | 1.0 | 1.0 | | | 2.0 | 2.0 | 1.0 | 1.0 | | |
| | Croscarmellose sodium | | | | | | | | | | | | |
| | Crystalline cellulose | | | | | | | | 4.0 | | | | |
| | Hydroxypropylmethylcellulose | | | | | 2.0 | | | | | | 2.0 | |
| | Purified water | 96.0 | 95.0 | 93.0 | 92.0 | 93.0 | 95.0 | 92.0 | 93.0 | 93.0 | 92.0 | 93.0 | 95.0 |
| Foaming property | | ++ | ++ | +++ | +++ | +++ | +++ | ++ | ++ | +++ | +++ | +++ | +++ |
| Persistence of gas bubbles | | +++ | +++ | +++ | +++ | +++ | +++ | +++ | +++ | +++ | +++ | +++ | +++ |

TABLE 21

| | Example | 239 | 240 | 241 | 242 | 243 | 244 | 245 | 246 | 247 | 248 | 249 |
|---|---|---|---|---|---|---|---|---|---|---|---|---|
| Composite | <<Carbonate>> | | | | | | | | | | | |
| granule of | Sodium bicarbonate | 2.4 | 2.4 | 2.4 | 2.4 | | | | | | 1.2 | 1.2 |
| carbonate | Sodium carbonate | | | | | 2.4 | 2.4 | 2.4 | 2.4 | 2.4 | 1.2 | 1.2 |
| and acid | <<Acid>> | | | | | | | | | | | |
| | Citric acid | | | | | 2.0 | | | | | 1.0 | |
| | Succinic acid | 2.0 | | | | | 2.0 | | | | 1.0 | |
| | Tartaric acid | | 2.0 | | | | | 2.0 | | | | 1.0 |
| | Lactic acid | | | 2.0 | | | | | 2.0 | | | 1.0 |
| | Potassium dihydrogenphosphate | | | | 2.0 | | | | | 2.0 | | |
| | <<Matrix base>> | | | | | | | | | | | |
| | Erythritol | | | | | 1.0 | 1.0 | 1.0 | 1.0 | 1.0 | | |
| | Carboxymethyl starch sodium | | | | | 1.0 | 1.0 | 1.0 | 1.0 | 1.0 | | |
| | Xylitol | 2.0 | 2.0 | 2.0 | 2.0 | | | | | | | |
| | Sorbitol | | | | | | | | | | 2.0 | |
| | Mannose | | | | | | | | | | | 2.0 |
| Aqueous | <<Thickener>> | | | | | | | | | | | |
| viscous | Sodium alginate | 2.0 | 2.0 | 2.0 | 2.0 | | | | | | 3.0 | 3.0 |
| composition | Carboxyvinyl polymer | | | | | 1.0 | 1.0 | 1.0 | 1.0 | 1.0 | | |
| | Carboxymethyl starch sodium | 2.5 | 2.5 | 2.5 | 2.5 | | | | | | | 2.0 |
| | Sodium carboxymethylcellulose | | | | | 3.0 | 3.0 | 3.0 | 3.0 | 3.0 | | |
| | Xanthan gum | 2.5 | 2.5 | 2.5 | 2.5 | | | | | | | |
| | Croscarmellose sodium | | | | | 2.0 | 2.0 | 2.0 | 2.0 | 2.0 | | |
| | Hydroxypropylcellulose | | | | | | | | | | 1.0 | |
| | Hydroxypropylmethylcellulose | | | | | | | | | | | 2.0 |
| | Polyvinyl alcohol | | | | | | | | | | 1.0 | |
| | Purified water | 93.0 | 93.0 | 93.0 | 93.0 | 94.0 | 94.0 | 94.0 | 94.0 | 94.0 | 95.0 | 93.0 |
| Foaming property | | +++ | +++ | +++ | ++ | +++ | +++ | +++ | +++ | ++ | +++ | +++ |
| Persistence of gas bubbles | | +++ | +++ | +++ | +++ | +++ | +++ | +++ | +++ | +++ | +++ | +++ |

EXAMPLES 250–272

Tables 22 and 23 show carbon dioxide-containing viscous compositions each prepared by bringing a carbonate-containing aqueous viscous composition into contact with an acid-containing sheet.

Production Process

Carbonate-containing aqueous viscous compositions and acid-containing sheets are prepared combining carbonates, acids (organic acids and/or an inorganic acid), thickeners, matrix bases and purified water as shown in Tables 22 and 23. The carbonate-containing aqueous viscous composition is brought into contact with the acid-containing sheet to provide a carbon dioxide-containing viscous composition.

<Preparation of the Carbonate-containing Aqueous Viscous Compositions>

The carbonate-containing aqueous viscous compositions are prepared in accordance with the process for preparation of carbonate-containing aqueous viscous compositions as described in Examples 1–84.

<Production of the Acid-containing Sheets>

The matrix base or bases are dissolved or dispersed in a solvent such as water or ethanol in a container such as a beaker. The acid is dissolved or dispersed therein. The resulting solution or dispersion is spread on a grass plate and extended to an adequate size to achieve a uniform thickness and then dried with an oven, etc. to provide an acid-containing sheet. If necessary, suitable additives and medicinal substances may be added. A nonwoven or woven fabric, a polymer film or the like may be used as a supporting material by applying an adhesive to the surrounding edge of the supporting material.

Evaluation of the Carbon Dioxide-containing Viscous Compositions

<Foaming Property>

50 g of the carbonate-containing aqueous viscous composition is placed on a glass plate and extended to a square (10 cm×10 cm) having a uniform thickness. Thereon is placed a square-shaped (10 cm×10 cm), acid-containing sheet containing 1 g of acid. Five minutes later, the resulting carbon dioxide-containing viscous composition is evaluated for its foaming property according to the following criteria:

"Good": bubbles are seen on the interface between the sheet and the aqueous viscous composition;

"None": no bubbles are seen on the interface between the sheet and the aqueous viscous composition.

<Persistence of Gas Bubbles>

50 g of the carbonate-containing aqueous viscous composition is placed on a glass plate and extended to a square (10 cm×10 cm) having a uniform thickness. Thereon is placed a square-shaped (10 cm×10 cm), acid-containing sheet containing 1 g of acid. The resulting carbon dioxide-containing viscous composition is evaluated for the persistence of gas bubbles according to the following criteria:

"Yes": both five minutes later and two hours later, gas bubbles are seen on the interface between the sheet and the aqueous viscous composition;

"No": gas bubbles are seen five minutes later but not seen two hours later.

TABLE 22

| | Example | 250 | 251 | 252 | 253 | 254 | 255 | 256 | 257 | 258 | 259 | 260 | 261 |
|---|---|---|---|---|---|---|---|---|---|---|---|---|---|
| Carbonate-containing | Sodium bicarbonate | 2.4 | 2.4 | 2.4 | 2.4 | 2.4 | 2.4 | 2.4 | 2.4 | 2.4 | 2.4 | 2.4 | 2.4 |
| | <<Thickener>> | | | | | | | | | | | | |
| viscous composition | Sodium alginate | 4.0 | 4.0 | 3.0 | 3.0 | 3.0 | 2.0 | 2.0 | 2.0 | 2.0 | 1.0 | 1.0 | 1.0 |
| | Carboxymethyl starch sodium | | | 1.0 | 2.0 | | 3.0 | | | 3.0 | 2.0 | | |
| | Sodium carboxymethylcellulose | | 1.0 | 2.0 | | 2.0 | 4.0 | | | | 3.0 | 2.0 | 2.0 |
| | Xanthan gum | | | | 1.0 | | | | 2.0 | 2.0 | | | |
| | Croscarmellose sodium | | | | | | 2.0 | | | | | | |
| | Crystalline cellulose | | | | | | | | 4.0 | | | | |
| | Hydroxypropylcellulose | | | | | | | | | | | 2.0 | 2.0 |
| | Hydroxypropylmethylcellulose | | | | | 2.0 | | | | | | | |
| | Bentonite | | | | | | | 4.0 | | | | | |
| | Polyvinyl alcohol | | | | | | | 2.0 | | | | | |
| | Purified water | 93.6 | 92.6 | 91.6 | 91.6 | 90.6 | 86.6 | 89.6 | 89.6 | 90.6 | 91.6 | 92.6 | 92.6 |
| Acid-containing | Citric acid | 2.0 | 2.0 | 2.0 | 2.0 | 2.0 | 2.0 | 2.0 | 2.0 | 2.0 | 2.0 | 2.0 | 2.0 |
| | <<Matrix base>> | | | | | | | | | | | | |
| sheet | Eudragit S | 2.0 | 2.0 | 2.0 | | | | 2.0 | | 2.0 | | | |
| | Eudragit RS | | | | 2.0 | 2.0 | 2.0 | | 2.0 | | 2.0 | | |
| | Hydroxypropylcellulose | | | | | | | | | | | | |
| | Triacetin | | | | | | | | 1.0 | 1.0 | | | |
| | Polyvinyl alcohol | | | | | | | | | | | 2.0 | 2.0 |
| Foaming property | | Good | Good | Good | Good | Good | Good | Good | Good | Good | Good | Good | Good |
| Persistence of gas bubbles | | Yes | Yes | Yes | Yes | Yes | Yes | Yes | Yes | Yes | Yes | Yes | Yes |

TABLE 23

| | Example | 262 | 263 | 264 | 265 | 266 | 267 | 268 | 269 | 270 | 271 | 272 |
|---|---|---|---|---|---|---|---|---|---|---|---|---|
| Carbonate- | <<Carbonate>> | | | | | | | | | | | |
| containing viscous composition | Sodium bicarbonate | 2.4 | 2.4 | 2.4 | 2.4 | | | | | | 1.2 | 1.2 |
| | Sodium carbonate | | | | | 2.4 | 2.4 | 2.4 | 2.4 | 2.4 | 1.2 | 1.2 |
| | <<Thickener>> | | | | | | | | | | | |
| | Sodium alginate | 2.0 | 2.0 | 2.0 | 2.0 | | | | | | 2.0 | 2.0 |
| | Ethyl cellulose | | | | | | | | | | | |
| | Carboxyvinyl polymer | | | | | 1.0 | 1.0 | 1.0 | 1.0 | 1.0 | | |
| | Carboxymethyl starch sodium | 2.0 | 2.0 | 2.0 | 2.0 | | | | | | 2.5 | 2.5 |
| | Sodium carboxymethylcellulose | 2.0 | 2.0 | 2.0 | 2.0 | 3.0 | 3.0 | 3.0 | 3.0 | 3.0 | 2.5 | 2.5 |
| | Xanthan gum | | | | | | | | | | | |
| | Croscarmellose sodium | | | | | 2.0 | 2.0 | 2.0 | 2.0 | 2.0 | | |
| | Purified water | 91.6 | 91.6 | 91.6 | 91.6 | 91.6 | 91.6 | 91.6 | 91.6 | 91.6 | 90.6 | 90.6 |
| Acid- | <<Acid>> | | | | | | | | | | | |
| containing sheet | Citric acid | | | | | 2.0 | | | | | 1.0 | |
| | Succinic acid | 2.0 | | | | | 2.0 | | | | 1.0 | |
| | Tartaric acid | | 2.0 | | | | | 2.0 | | | | 1.0 |
| | Lactic acid | | | 2.0 | | | | | 2.0 | | | 1.0 |
| | Potassium dihydrogenphosphate | | | | 2.0 | | | | | 2.0 | | |

TABLE 23-continued

| Example | | 262 | 263 | 264 | 265 | 266 | 267 | 268 | 269 | 270 | 271 | 272 |
|---|---|---|---|---|---|---|---|---|---|---|---|---|
| <<Matrix base>> | | | | | | | | | | | | |
| | Eudragit S | 2.0 | 2.0 | 2.0 | 2.0 | | | | | | | |
| | Eudragit RS | | | | | 2.0 | 2.0 | 2.0 | 2.0 | 2.0 | 2.0 | 2.0 |
| Foaming property | | Good | Good | Good | Good | Good | Good | Good | Good | Good | Good | Good |
| Persistence of gas bubbles | | Yes | Yes | Yes | Yes | Yes | Yes | Yes | Yes | Yes | Yes | Yes |

EXAMPLES 273–294

Tables 24 and 25 show carbon dioxide-containing viscous compositions each prepared by bringing an acid-containing aqueous viscous composition into contact with a carbonate-containing sheet.

Production Process

Acid-containing aqueous viscous compositions and carbonate-containing sheets are prepared combining carbonates, acids (organic acids and/or an inorganic acid), thickeners, matrix bases and purified water as shown in Tables 24 and 25. The acid-containing aqueous viscous composition is brought into contact with the carbonate-containing sheet to provide a carbon dioxide-containing viscous composition.

<Preparation of the Acid-containing Aqueous Viscous Compositions>

The acid-containing aqueous viscous compositions are prepared in accordance with the process for preparation of acid-containing aqueous viscous compositions as described in Examples 85–108.

<Preparation of the Carbonate-containing Sheets>

The matrix base or bases are dissolved or dispersed in a solvent such as water or ethanol in a container such as a beaker. The carbonate is dissolved or dispersed therein. The resulting solution or dispersion is spread on a glass plate and extended to an adequate size to achieve a uniform thickness and then dried with an oven, etc. to provide a carbonate-containing sheet. If necessary, suitable additives and medicinal substances may be added. A nonwoven or woven fabric, a polymer film or the like may be used as a supporting material by applying an adhesive to the surrounding edge of the supporting material.

Evaluation of the Carbon Dioxide-containing Viscous Compositions

<Foaming Property>

50 g of the acid-containing aqueous viscous composition is placed on a glass plate and extended to a square (10 cm×10 cm) having a uniform thickness. Thereon is placed a square-shaped (10 cm×10 cm), carbonate-containing sheet containing 1.2 g of carbonate. Five minutes later, the resulting carbon dioxide-containing viscous composition is evaluated for its foaming property according to the following criteria:

"Good": bubbles are seen on the interface between the sheet and the aqueous viscous composition;

"None": no bubbles are seen on the interface between the sheet and the aqueous viscous composition.

<Persistence of Gas Bubbles>

50 g of the acid-containing aqueous viscous composition is placed on a glass plate and extended to a square (10 cm×10 cm) having a uniform thickness. Thereon is placed a square-shaped (10 cm×10 cm), carbonate-containing sheet containing 1.2 g of carbonate. The resulting carbon dioxide-containing viscous composition is evaluated for the persistence of gas bubbles according to the following criteria:

"Yes": both five minutes later and two hours later, gas bubbles are seen on the interface between the sheet and the aqueous viscous composition;

"No": gas bubbles are seen five minutes later but not seen two hours later.

TABLE 24

| | Example | 273 | 274 | 275 | 276 | 277 | 278 | 279 | 280 | 281 | 282 | 283 |
|---|---|---|---|---|---|---|---|---|---|---|---|---|
| Acid-containing | Citric acid | 2.0 | 2.0 | 2.0 | 2.0 | 2.0 | 2.0 | 2.0 | 2.0 | 2.0 | 2.0 | 2.0 |
| | <<Thickener>> | | | | | | | | | | | |
| viscous | Sodium alginate | 4.0 | 4.0 | 3.0 | 3.0 | 3.0 | 2.0 | 2.0 | 2.0 | 2.0 | 1.0 | 1.0 |
| composition | Carboxymethyl starch sodium | | | 1.0 | 2.0 | | 3.0 | | | 3.0 | 2.0 | |
| | Sodium carboxymethylcellulose | | 1.0 | 2.0 | | 2.0 | 4.0 | | | | 3.0 | 2.0 |
| | Xanthan gum | | | | 1.0 | | | | 2.0 | 2.0 | | |
| | Croscarmellose sodium | | | | | | 2.0 | | | | | |
| | Crystalline cellulose | | | | | | | | 4.0 | | | |
| | Hydroxypropylcellulose | | | | | | | | | | | 2.0 |
| | Hydroxypropylmethylcellulose | | | | | | 2.0 | | | | | |
| | Bentonite | | | | | | | 4.0 | | | | |
| | Polyvinyl alcohol | | | | | | | 2.0 | | | | |
| | Purified water | 94.0 | 93.0 | 92.0 | 92.0 | 91.0 | 87.0 | 90.0 | 90.0 | 91.0 | 92.0 | 93.0 |
| Carbonate-containing | Sodium bicarbonate | 2.4 | 2.4 | 2.4 | 2.4 | 2.4 | 2.4 | 2.4 | 2.4 | 2.4 | 2.4 | 2.4 |
| | <<Matrix base>> | | | | | | | | | | | |
| sheet | Eudragit S | 2.4 | 2.4 | 2.4 | | | | 2.4 | | 2.4 | | |
| | Eudragit RS | | | | 2.4 | 2.4 | 2.4 | | 2.4 | | 2.4 | |
| | Hydroxypropylcellulose | | | | | | | | | | | |
| | Triacetin | | | | | | | 0.2 | 0.2 | | | |
| | Polyvinyl alcohol | | | | | | | | | | | 2.4 |

TABLE 24-continued

| Example | 273 | 274 | 275 | 276 | 277 | 278 | 279 | 280 | 281 | 282 | 283 |
|---|---|---|---|---|---|---|---|---|---|---|---|
| Foaming property | Good | Good | Good | Good | Good | Good | Good | Good | Good | Good | Good |
| Persistence of gas bubbles | Yes | Yes | Yes | Yes | Yes | Yes | Yes | Yes | Yes | Yes | Yes |

TABLE 25

| | Example | 284 | 285 | 286 | 287 | 288 | 289 | 290 | 291 | 292 | 293 | 294 |
|---|---|---|---|---|---|---|---|---|---|---|---|---|
| Acid- | <<Acid>> | | | | | | | | | | | |
| containing | Citric acid | | | | | 2.0 | | | | | 1.0 | |
| viscous | Succinic acid | 2.0 | | | | | 2.0 | | | | 1.0 | |
| composition | Tartaric acid | | 2.0 | | | | | 2.0 | | | | 1.0 |
| | Lactic acid | | | 2.0 | | | | | 2.0 | | | 1.0 |
| | Potassium dihydrogenphosphate | | | | 2.0 | | | | | 2.0 | | |
| | <<Thickener>> | | | | | | | | | | | |
| | Sodium alginate | 2.0 | 2.0 | 2.0 | 2.0 | | | | | | 2.0 | 2.0 |
| | Ethyl cellulose | | | | | 1.0 | 1.0 | 1.0 | 1.0 | 1.0 | | |
| | Carboxyvinyl polymer | 2.0 | 2.0 | 2.0 | 2.0 | | | | | | 2.0 | 2.0 |
| | Carboxymethyl starch sodium | 3.0 | 3.0 | 3.0 | 3.0 | | | | | | 3.0 | 3.0 |
| | Sodium carboxymethylcellulose | | | | | 1.0 | 1.0 | 1.0 | 1.0 | 1.0 | | |
| | Xanthan gum | | | | | 2.0 | 2.0 | 2.0 | 2.0 | 2.0 | | |
| | Croscarmellose sodium | | | | | 1.0 | 1.0 | 1.0 | 1.0 | 1.0 | | |
| | Purified water | 91.0 | 91.0 | 91.0 | 91.0 | 93.0 | 93.0 | 93.0 | 93.0 | 93.0 | 91.0 | 91.0 |
| Carbonate- | <<Carbonate>> | | | | | | | | | | | |
| containing | Sodium bicarbonate | 2.4 | 2.4 | 2.4 | 2.4 | | | | | | 2.4 | 2.4 |
| sheet | Sodium carbonate | | | | | 2.4 | 2.4 | 2.4 | 2.4 | 2.4 | | |
| | <<Matrix base>> | | | | | | | | | | | |
| | Eudragit S | 2.4 | 2.4 | 2.4 | | | | | | | 2.4 | 2.4 |
| | Eudragit RS | | | | 2.4 | 2.4 | 2.4 | 2.4 | 2.4 | 2.4 | | |
| Foaming property | | Good | Good | Good | Good | Good | Good | Good | Good | Good | Good | Good |
| Persistence of gas bubbles | | Yes | Yes | Yes | Yes | Yes | Yes | Yes | Yes | Yes | Yes | Yes |

EXAMPLE 295

A Carbon Dioxide-containing Viscous Composition for Occlusive Therapy Prepared by Mixing a Carbonate, an Acid and an Aqueous Viscous Composition Production Process 0.24 g of sodium bicarbonate is mixed with 0.2 g of citric acid. The mixture is placed on the adhesive face of a film dressing (trade name: "Tegaderm", product of 3M company), 6 cm×7 cm, and evenly spread 2 cm inside from the edge of the adhesive face. A thin nonwoven fabric, 5 cm×6 cm, is placed thereon and attached to the adhesive face of the dressing film so that the mixture of sodium bicarbonate and citric acid does not spill. An aqueous viscous composition containing 0.3 g of sodium alginate, 0.2 g of sodium carboxymethylcellulose and 9.5 g of purified water is prepared in accordance with the production method described in <Preparation of the aqueous viscous compositions> in Examples 227–249. The composition is applied to the nonwoven fabric so as to evenly spread 1 cm inside from the edge of the nonwoven fabric, thus providing a carbon dioxide-containing viscous composition for occlusive therapy.

EXAMPLE 296

A Carbon Dioxide-containing Viscous Composition for Occlusive Therapy Prepared by Mixing a Composite Granule of Carbonate and Acid and an Aqueous Viscous Composition Production Process 5 g of cetanol is melted in a 100-ml beaker using a hot bath. Thereto were added 24 g of sodium bicarbonate and 20 g of citric acid, and the mixture is fully stirred. The mixture is further stirred while being gradually cooled at room temperature. When the mixture solidifies to some extent, stirring is stopped and the mixture is allowed to stand until it completely solidifies. When the residue completely solidifies, the solid is pulverized to provide a composite granule of carbonate and acid.

0.49 g of the composite granule is placed on the adhesive face of a film dressing (trade name: "Tegaderm", product of 3M company), 6 cm×7 cm, and thinly spread 2 cm inside from the edge of the adhesive face. A thin nonwoven fabric, 5 cm×6 cm, is placed thereon and attached to the adhesive face of the dressing film so that the composite granule does not spill. An aqueous viscous composition containing 0.3 g of sodium alginate, 0.2 g of sodium carboxymethylcellulose and 9.5 g of purified water is prepared in accordance with the production method described in <Preparation of the aqueous viscous compositions> in Examples 227–249. The composition is applied to the nonwoven fabric so as to evenly spread 1 cm inside from the edge of the nonwoven fabric, thus providing a carbon dioxide-containing viscous composition for occlusive therapy.

EXAMPLE 297

A Carbon Dioxide-containing Viscous Composition Prepared by Mixing a Carbonate-containing Aqueous Viscous Composition and an Acid Coated Granule A carbonate-containing aqueous viscous composition and an acid coated granule are mixed with stirring to provide a carbon dioxide-containing viscous composition. The mixing ratio may be suitably selected. In Test Examples 22–25 shown below, the acid coated granule containing 1 part by weight of acid is used per the carbonate-containing aqueous viscous composition containing 1.2 parts by weight of carbonate.

<Preparation of the Carbonate-containing Aqueous Viscous Composition>

2 g of methylparaben, 24 g of sodium bicarbonate, 40 g of carboxymethyl starch sodium, 40 g of sodium alginate and 40 g of sodium carboxymethylcellulose are dissolved or dispersed in 2,000 ml of water and fully stirred to provide a carbonate-containing aqueous viscous composition. If necessary, suitable additives and medicinal substances may be added.

<Preparation of the Acid Coated Granule>

A solution of 1.8 kg of citric acid in 722 g of a 7% HPC-L ethanol solution was sprayed over 9 kg of purified sucrose granules (trade name: "Nonpareil 103", product of Freund Industrial Co., Ltd.) using a CF granulator by a conventional method. After drying, 10.7 kg of an acid coated granule was obtained.

EXAMPLE 298

A Carbon Dioxide-containing Viscous Composition Prepared by Mixing a Carbonate- and Plant Essential Oil-containing Aqueous Viscous Composition and an Acid Coated Granule Production Process The following components are dissolved or dispersed in 1000 ml of water and fully stirred.

| | |
|---|---|
| Methylparaben | 1 g |
| Sodium bicarbonate | 12 g |
| Carboxymethyl starch sodium | 25 g |
| Sodium alginate | 20 g |
| Sodium carboxymethylcellulose | 25 g |
| Grapefruit oil | 0.5 ml |
| Cajeput oil | 0.1 ml |
| Rosewood oil | 0.1 ml |
| Geranium oil | 0.1 ml |
| Food Green | 0.01 g |
| Alpha-tocopherol acetate | 1 ml |

If necessary, suitable additives and medicinal substances may be added. Added to 25 g of the solution or dispersion is 1.2 g of the acid coated granule obtained in Example 297, followed by stirring to provide a cream of a carbon dioxide-containing viscous composition.

EXAMPLE 299

A Carbon Dioxide-containing Viscous Composition Prepared by Blowing Carbon Dioxide Into an Aqueous Viscous Composition Production Process 12 g of sodium bicarbonate, 20 g of carboxymethyl starch sodium and 20 g of sodium alginate are dissolved in 1000 ml of water to provide an aqueous viscous composition. Immersed in the composition is an end of a vinyl tube (6.0 mm in outer diameter, 3.5 mm in inner diameter and 60 cm long) connected to a small carbon dioxide bomb (trade name: "Tetra $CO_2$ bomb", product of Warner-Lambert Company). While carbon dioxide is blown into the composition, 20 g of carboxymethylcellulose is added and dissolved with stirring to provide a carbon dioxide-containing viscous composition.

TEST EXAMPLE 1

Therapeutic Trial on Itching Associated With Athlete's Foot

A 41 year-old male. His right foot with athlete's foot accompanying severe itching was soaked in 100 g of the composition of Example 8 in a wash basin for about 20 minutes. One treatment with the composition of the invention stopped itching.

TEXT EXAMPLE 2

Therapeutic Trial on Itching Associated With Athlete's Foot

A 73 year-old female. Her both feet with athlete's foot accompanying extremely severe itching were soaked in 300 g of the composition of Example 18 in a wash basin for about 20 minutes. Two-year treatment with an antifungal agent for external use had produced no therapeutic effects, but one treatment with the composition of the invention stopped itching.

TEXT EXAMPLE 3

Therapeutic Trial on Angular Stomatitis

A 41 year-old male. 1 g of the composition of Example 8 was applied to angular stomatitis for 10 minutes. The pain disappeared and the wound was closed and healed.

TEXT EXAMPLE 4

Therapeutic Trial on Decubitus Ulcer

A 78 year-old male. He became bedridden with the progress of lung cancer, and a decubitus ulcer developed from the lumbar region to the hip. The ulcer was about 4 cm deep and reached the fascia. 100 g of the composition of Example 1 was filled in the pocket of the ulcer and covered with a film dressing, 20 cm×30 cm, (trade name: "Tegaderm", product of 3M company) for 20 minutes. The composition and the film dressing were replaced with new ones every day. On the 11th day of the treatment, the ulcer became 1 cm deep. One month after the start of treatment, the benign granulation tissues grew up almost to the same level as the normal skin around the granulation tissues.

TEXT EXAMPLE 5

Therapeutic Trial on Canvas Shoe Dermatitis

An 8 year-old male. He was bleeding at the soles due to canvas shoe dermatitis. A steroidal ointment (trade name: "Rinderon V", product of Shionogi & Co., Ltd.) was applied for 2 months but was ineffective. 30 g of the composition of Example 20 was applied to his soles. The wound was closed on day 4 and completely healed in 1 month.

TEST EXAMPLE 6

Trial on Hair Glossiness

A 41 year-old male. He was worried about loss of hair glossiness and looking old, and applied 20 g of the composition of Example 18 to the hair for about 15 minutes once a day. On and after the third day, hair glossiness increased.

TEST EXAMPLE 7

Therapeutic Trial on Atopic Dermatitis

A 4 year-old female. To treat atopic dermatitis at the back of her knees, 5 g of the composition of Example 20 was applied for 5 minutes once a day. The darkness of the skin faded away in 2 weeks and dry skin healed in 4 weeks.

TEST EXAMPLE 8

Trial on Partial Slimming of the Face and Abdomen

A 41 year-old male. With the hope of slimming full cheeks and thick waist, he applied 30 g of the composition of Example 8 to the right cheek and 100 g of the same to the abdomen for 15 minutes once a day. Two months later, all the five evaluators judged that his right cheek obviously became smaller. His waist size decreased by 6 cm.

TEST EXAMPLE 9

Trial on Skin Quality Improvement and Face Slimming

A 37 year-old female. She was worried about full cheeks, rough skin and faded skin complexion and tested various cosmetics, but all were ineffective. She applied 50 g of the composition of Example 20 to the entire face for 10 minutes once a day. With the first application, faded skin complexion improved and her skin became white and had a fine skin texture. Two weeks later, all the three evaluators judged that her face became smaller.

TEST EXAMPLE 10

Therapeutic trial on Cervico-omo-brachial Syndrome

A 42 year-old male. To treat cervico-omo-brachial syndrome (a shoulder stiffness) caused by fatigue resulting from computer operations, an antiinflammatory agent for external use (trade name: "Tiger Balm", product of Haw Par Healthcare Ltd.) was applied but produced no effects. By applying 40 g of the composition of Example 20 to the shoulders for 20 minutes, cervico-omo-brachial syndrome cured.

TEST EXAMPLE 11

Therapeutic Trial on Psoriasis Vulgaris

A 37 year-old female. Her knee with psoriasis vulgaris accompanying extremely severe itching was treated by applying 3 g of the composition of Example 20 for 10 minutes once a day. With the first application, itching disappeared. Two weeks later, darkness of the lesion lessened.

TEST EXAMPLE 12

Therapeutic Trial in a Corn

A 37 year-old female. To treat a corn on the right side of her left foot little finger accompanying pain, 2 g of the composition of Example 20 was applied for 10 minutes once a day for 5 days. Corn healed without damaging the normal skin around the corn, unlike salicylic acid pharmaceuticals.

TEST EXAMPLE 13

Trial on Partial Slimming of Arms

A 36 year-old female. She was worried about thick upper arms. 30 g of the composition of Example 18 was applied to her left upper arm and wrapped with a film for food packaging (trade name: "Saran Wrap", product of Asahi Chemical Industry Co., Ltd.) and allowed to stand for 6 hours. Her arm circumference decreased by 2 cm.

TESTS EXAMPLE 14

Therapeutic Trial on Suppurative Eczema on the Hip

A 29 year-old male. To treat suppurative eczema over the entire hip, 40 g of the composition of Example 18 was applied for 20 minutes once a day for 7 days. Suppurative eczema healed.

TEST EXAMPLE 15

Therapeutic Trial on Insect Bite Itch

A 51 year-old female. A bee stung her on the arm and hand finger. Local swelling and flare subsided by administration of an antihistamine (trade name: "Celestamine tablet", product of Schering-Plough Corporation) and application of a steroidal ointment (trade name: "Terra-Cortril Ointment", product of Pfizer Inc.). However, itching started and gradually increased so that she suffered insomnia 2 weeks later. With the application of 5 g of the composition of Example 18 for 15 minutes, itching disappeared and she had a good sleep.

TEXT EXAMPLE 16

Therapeutic Trial on Itching Associated With Athlete's Foot

A 32 year-old female. To treat athlete's foot accompanying extremely severe itching on her both feet, an antifungal drug (trade name: "Mentax cream", product of Kaken Pharmaceutical Co., Ltd.) was applied for 2 months but did not alleviate the itching at all. Her feet were soaked in 100 g of the composition of Example 8 in a wash basin for about 20 minutes. With the first treatment, itching disappeared. Four days later, her feet were soaked again in 100 ml of the composition of Example 8 in a wash basin for about 20 minutes. Remarkable improvement in the lesion was observed by the naked eye.

TEXT EXAMPLE 17

Therapeutic Trial on Palmoplantar Pustulosis

A 22 year-old female. To treat palmoplantar pustulosis accompanying extremely severe itching on her hands, both hands were soaked in 100 g of the composition of example 18 in a wash basin for about 15 minutes. Itching disappeared instantly.

TEXT EXAMPLE 18

Therapeutic Trial on Atopic Dermatitis

An 8 year-old male. To treat atopic dermatitis on the fingers with extremely severe itch and pain accompanying partially keratinized and cracked skin, his fingertips were soaked in 50 g of the composition of Example 8 in a cup for 20 minutes. Itching disappeared instantly. On the following day, new epithelium was observed on the cracked skin, and pain eased.

TEXT EXAMPLE 19

Therapeutic Trial on Psoriasis Vulgaris

A 37 year-old male. To treat psoriasis vulgaris on the knees accompanying extremely severe itch, 10.49 g of the composition of Example 296 was applied for 30 minutes. Itching disappeared instantly. Keratinized, dry skin on the lesion was remarkably improved.

TEXT EXAMPLE 20

Therapeutic Trial on Facial Abrasion

A 10 year-old male. To treat an abrasion, 3 cm×4 cm, on the right side of his face, 10.49 g of the composition of Example 296 was applied. The composition was newly applied once a day. On day 2, re-epithelization was observed without crust formation. On day 5, the wound was healed without scar.

TEXT EXAMPLE 21

Dry Skin Pruritus

A 69 year-old male. To treat dry skin pruritus on both lower legs, 50 g of the composition of Example 20 was applied and wrapped with a film for food packaging (trade name "Saran Wrap", product of Asahi Chemical Industry Co., Ltd.). Itching disappeared.

TEXT EXAMPLE 22

Therapeutic Trial on Decubitus Ulcer

A 65 year-old male. He had been in a vegetative state since postoperation of removing a hematoma due to intracerebral bleeding. A decubitus ulcer of level 4 (15 cm×15 cm) was formed in the sacral region to reach the periosteum. Recognized on the wound surface were necrotic tissues adhering to the surface, a deep pocket and exudate. The wound surface was washed with physiological saline, and povidone-iodine sugar was applied but such treatment hardly produced any effects. 30 g of the carbon dioxide-containing viscous composition of Example 297 was filled in the pocket of the decubitus ulcer and further applied in a heap to the wound surface once a day. A film dressing, 20 cm×30 cm, (trade name: "Tegaderm", product of 3M company) was applied thereon. The composition and the film dressing were replaced with new ones every day. On the 5th day of the application of the composition, necrotic tissues and exudate disappeared from the wound surface, and a rapid healing tendency was shown. At the same time, increase of benign granulation tissues was recognized. In two months, size and depth of the decubitus ulcer were remarkably reduced, epithelium was formed on the wound surface, and the pocket disappeared.

TEXT EXAMPLE 23

Therapeutic Trial on Alveolar Pyorrhea

A 28 year-old female. Swelling and flare of the gingiva were severe and her gum tissue reached the root of the teeth. The periodontal pocket was scaled and 30 g of the carbon dioxide-containing viscous composition of Example 297 was injected into the periodontal pocket and further applied to cover the whole gingiva for 20 minutes every two days. One month later, the swelling and redness of the gingiva were almost completely relieved.

TEXT EXAMPLE 24

Therapeutic Trial on Labial Laceration

A 7 year-old female. She inadvertently bit her lower lip with her maxilla front teeth and received a traumatic laceration with the trace of the teeth remaining on the lip. 5 g of the carbon dioxide-containing viscous composition of Example 297 was applied for 20 minutes. The wound healed so that substantially no scar was left.

TEXT EXAMPLE 25

Therapeutic Trial on Denture Ulcer

A 67 year-old female. After she wore non-fitting dentures, ulcers developed with pain on the mucosa under the denture bases. The dentures were removed to cut the marginal regions and improve the fitting. On the other hand, 5 g of the carbon dioxide-containing viscous composition of Example 297 was applied to the ulcers, and then the dentures were worn again. On the medical examination 5 days later, the ulcers had disappeared.

TEXT EXAMPLE 26

Test on Freckles

A 38 year-old female. She suffered from freckles for many years and used various cosmetics in vain. 26.2 g of the carbon dioxide-containing viscous composition of Example 298 was applied to her whole face for 20 minutes once a day. On day 3, her freckles faded so remarkably that moles stood out.

TEXT EXAMPLE 27

Therapeutic Trial on Stomatitis

A 43 year-old male. To treat stomatitis accompanying pain on the right palate, 3 g of the composition of Example 170 was applied for 20 minutes. The pain disappeared instantly.

TEXT EXAMPLE 28

Therapeutic Trial on Impetigo

A 4 year-old female. To treat impetigo on her right upper arm, 10 g of the composition of Example 297 was applied for 20 minutes and then a proper amount of sodium fusidate (trade name: "Fucidin Leo ointment", product of Sankyo Company, Limited) was applied once a day. On day 5, impetigo healed without scar formation.

TEXT EXAMPLE 29

Therapeutic Trial on Acne Vulgaris

A 28 year-old female. To treat acne vulgaris all over the face, various non-steroidal anti-inflammatory agents and oral antibiotics were tested but were not effective at all. 30 g of the composition of Example 297 was applied for 30 minutes once a day. In two months, papules became flattened and only flare was slightly left.

TEXT EXAMPLE 30

Therapeutic Trial on Lower Limb Skin Ulcer

A 63 year-old female. To treat a skin ulcer 1 cm in diameter and punctate erosion caused by lower limb varix, 15 g of the composition of Example 297 was applied for 20 minutes once a day. With the first application, erosion disappeared and healed. On day 10, the administration of the composition was stopped because skin ulcer remarkably diminished. On the following day, crust formation was observed and ulcer healed.

TEXT EXAMPLE 31

Therapeutic Trial on lower limb Cryesthesia, Pruritus, Numbness

A 71 year-old male. To treat cryesthesia, pruritus and numbness in his lower limbs caused by peripheral circulatory disorders, 30 g of the composition of Example 31 was applied to the lower limbs for 20 minutes once a week. With the application of the composition seven times, all the symptoms disappeared.

TEXT EXAMPLE 32

Therapeutic Trial on Gingivitis

A 42 year-old male. To treat gingivitis with marked swelling and redness complicated by a severe toothache, 10 g of the composition of Example 297 was applied for 10 minutes three times a day on the first day and twice on the second day. With the first application, toothache disappeared and gingival swelling and redness were remarkably improved.

TEXT EXAMPLE 33

Trial on Suppression of Hair Re-growth After Depilation

A 38 year-old female. She had shaved unwanted hair under her arms with a razor twice a week and wished to reduce the frequency of shaving. 30 g of the composition of Example 135 (15 g each) was applied under her arms for 15 minutes once a day. One month later, re-growth of replacement hair was retarded after shaving unwanted hair under the arms, and shaving with a razor once a week became sufficient thereafter.

What is claimed is:

1. A carbon dioxide-containing aqueous composition comprising two or more thickeners and carbon dioxide, wherein the composition comprises the carbon dioxide in the form of bubbles in an amount of 10–80 vol % of the total composition, the carbon dioxide-containing composition being characterized in that the thickener is comprised in an amount of 2 wt % or more of the total composition and is at least two selected from the group consisting essentially of xanthan gum, ethyl cellulose, carboxymethyl cellulose and salts thereof, carboxymethylethyl cellulose and salts thereof, carboxymethyl starch and salts thereof, croscarmellose and salts thereof, crystalline cellulose, hydroxypropyl cellulose, hydroxypropylmethyl cellulose, sodium alginate, and carboxyvinyl polymer.

2. The carbon dioxide-containing composition according to claim 1, wherein the thickener is comprised in an amount of 4–8 wt % of the total composition, and water in an amount of 60–96 wt %.

3. The carbon dioxide-containing composition according to claim 1, which is characterized in that the thickener comprises carboxymethyl cellulose, salts thereof and sodium alginate.

4. The carbon dioxide-containing composition according to any one of claims 1–3 or the carbon dioxide-containing composition obtainable by a kit comprising a carbonate or carbonates, an acid or acids, a thickener or thickeners and water in a state where the components produce substantially no carbon dioxide, which kit produces a carbon dioxide-containing composition comprising carbon dioxide bubbles by mixing the carbonate or carbonates, the acid or acids, the thickener or thickeners and water.

5. The carbon dioxide-containing composition according to claim 4, being capable of reducing or attenuating freckles.

6. The carbon dioxide-containing composition according to claim 4, being capable of ameliorating partial obesities in at least one of the face, foot, arm, abdomen, latus, back, neck, and chin.

7. The carbon dioxide-containing composition according to claim 4, having an action of ameliorating skin complexion.

8. The carbon dioxide-containing composition according to claim 4, having an action of suppressing hair re-growth after depilation.

9. The carbon dioxide-containing composition according to claim 4, which comprises sodium alginate, sodium carboxymethyl cellulose, sodium bicarbonate, citric acid, ascorbic acid, 1,3-butylene glycol, and water.

10. The carbon dioxide-containing composition according to claim 4, which shows a decrease in volume of gas bubbles of 40% or less between one minute and two hours after 50 g of carbonate-containing aqueous composition and 1 g of acid are placed in cup 5 cm in diameter and 10 cm high and stirred 20 times for 10 seconds to produce the carbon dioxide-containing composition.

11. The carbon dioxide-containing composition according to claim 4, which shows an increase in volume of 50% or greater after one minute from stirring when 50 g of carbonate-containing aqueous composition and 1 g of acid are placed in cup 5 cm in diameter and 10 cm high and stirred 20 times for 10 seconds to produce the carbon dioxide-containing composition.

* * * * *